US010597801B2

(12) United States Patent
Montague

(10) Patent No.: US 10,597,801 B2
(45) Date of Patent: Mar. 24, 2020

(54) SHIRT CUTTING JIG AND PROCESS FOR CONVERTING SHIRTS INTO YARN

(71) Applicant: Jonathan A. Montague, Ardsley, NY (US)

(72) Inventor: Jonathan A. Montague, Ardsley, NY (US)

(*) Notice: Subject to any disclaimer, the term of this patent is extended or adjusted under 35 U.S.C. 154(b) by 0 days.

(21) Appl. No.: 16/574,304

(22) Filed: Sep. 18, 2019

(65) Prior Publication Data

US 2020/0010984 A1 Jan. 9, 2020

Related U.S. Application Data

(60) Provisional application No. 62/810,443, filed on Feb. 26, 2019.

(51) Int. Cl.
*D02G 3/06* (2006.01)
*D01G 11/04* (2006.01)

(52) U.S. Cl.
CPC ............... *D02G 3/06* (2013.01); *D01G 11/04* (2013.01)

(58) Field of Classification Search
CPC .......... D02G 3/06; D01G 11/04; B26F 1/3853
See application file for complete search history.

(56) References Cited

U.S. PATENT DOCUMENTS

| 2,187,574 | A | * | 1/1940 | Nigra | B43L 5/00 |
| | | | | | 33/430 |
| 2,790,498 | A | * | 4/1957 | Carscallen | B26D 1/045 |
| | | | | | 83/383 |
| 3,527,131 | A | * | 9/1970 | Ellerin | B26F 1/3853 |
| | | | | | 83/522.19 |
| 3,768,357 | A | * | 10/1973 | McBride | B26D 3/02 |
| | | | | | 83/438 |
| 4,038,751 | A | * | 8/1977 | Albright | B26F 1/3853 |
| | | | | | 30/293 |
| 4,226,098 | A | * | 10/1980 | Alexander | B26D 1/185 |
| | | | | | 69/2 |
| 5,264,067 | A | * | 11/1993 | Kuchta | B23Q 1/01 |
| | | | | | 156/361 |
| 5,277,092 | A | * | 1/1994 | Kinta | B26D 7/018 |
| | | | | | 210/253 |

(Continued)

OTHER PUBLICATIONS http://www.olin.edu/the-wire/2018/good-fit/ (Dec. 4, 2018).*

(Continued)

*Primary Examiner* — Shaun R Hurley
(74) *Attorney, Agent, or Firm* — Cowan, Liebowitz & Latman, P.C.

(57) ABSTRACT

A method/shirt cutting jig for converting a textile into yarn comprises mounting a tubular body of a textile on the jig's base, securing a first folded edge of the tubular body using a clamping bar and securing the second folded edge of the tubular body using a clamping panel. The clamping panel includes teeth that allow a user of the jig to cut the tubular body into strips of material fully past the second folded edge. A movable cutting fence enables the user to cut the tubular body into multiple strips of material, but where each cut does not extend fully past the tubular body's first folded edge. The tubular body with the cuts is removed from the jig and then manually cut in a diagonal pattern along its first folded edge to produce a single strip of material that is then easily converted into reusable yarn.

15 Claims, 24 Drawing Sheets

(56) References Cited

U.S. PATENT DOCUMENTS

| | | | | |
|---|---|---|---|---|
| 5,277,093 A * | 1/1994 | Kinta | ............. | B26D 7/018 |
| | | | | 210/253 |
| 6,182,549 B1 * | 2/2001 | Albright | ............. | B26D 7/015 |
| | | | | 269/303 |
| 6,199,495 B1 * | 3/2001 | Schafer | ............. | D05C 17/00 |
| | | | | 112/409 |
| 6,895,675 B2 * | 5/2005 | Albright | ............. | B26B 29/06 |
| | | | | 33/418 |
| 7,464,480 B2 * | 12/2008 | Vetromila | ............. | G01B 3/04 |
| | | | | 33/1 G |
| 9,624,612 B2 * | 4/2017 | Works | ............. | D05B 97/12 |
| 2004/0143979 A1 * | 7/2004 | Albright | ............. | B26B 29/06 |
| | | | | 33/42 |
| 2015/0267334 A1 * | 9/2015 | Works | ............. | D05B 97/12 |
| | | | | 33/566 |

OTHER PUBLICATIONS

Potholder Loom: Basics and Beyond, by Syne Mitchell, 9 pages, May 8, 2009.
Look at What I Made—How to Make Fabric Yarn Article, 12 pages, Jan. 12, 2016.
How to Make a Woven Potholder, by A and J Hobby Workshop, 15 pages, 2018.
Spruce Crafts, How to Make T-Shirt Yarn, 14 pages, Dec. 8, 2018.
Svellerella, How to make your own T-shirt Yan, 22 pages, 2014.
Molli Makes, How to make t-shirt yarn for knitting or crochet, 12 pages, Mar. 12, 2018.
Hands Occupied, How to Make Fabric Yarn, 29 pages, Jul. 4, 2014.

* cited by examiner

SHIRT CUTTING JIG AND PROCESS FOR CONVERTING SHIRTS INTO YARN

REFERENCE TO RELATED APPLICATION

This application claims priority to U.S. Provisional Patent Application No. 62/810,443, filed Feb. 26, 2019, the disclosure of which is incorporated herein by reference.

BACKGROUND OF THE INVENTION

1. Field of the Invention

The present invention is directed to a machine and method of using that machine that facilitates the recycling of used (and unworn) T-shirts and similar textiles into other usable products. More particularly, the present invention is directed to a novel shirt cutting jig and process for using the shirt cutting jig to quickly and easily convert/recycle T-shirts (and similar products) into yarn that may then be used to create any number of products.

2. Description of the Related Art

Like most used products, the bulk of used clothing ends up in the countless landfills that exist in the United States and other countries. Globally, between 80% and 85% of used clothing and other textiles are doomed for the landfill or are incinerated.

The disadvantages of dumping used textiles are well known . . . natural fibers take hundreds of years or more to decompose, and the decomposing materials release methane and $CO_2$ gas into the atmosphere, as well as release toxic substances into groundwater and the surrounding soil. Recycling is the clear solution.

Textile recycling offers several environmental benefits. In addition to reducing landfill space requirements and the release of harmful components into the air, ground, and water, recycling textiles will reduce over time consumption of energy and water, lessen the demand for dyes, reduce the need for virgin resources (i.e., virgin fibers), encourage the development of additional markets, among other benefits.

OBJECTS AND SUMMARY OF THE INVENTION

In view of the foregoing, it is an object of the present invention to provide a machine, referred to herein as a shirt cutting jig, that allows a person to convert a T-shirt or similar textiles into usable yarn for use to manufacture any number of goods.

It is a further object of the invention to provide a shirt cutting jig that is affordable to manufacture and that is easy to use. It is another object of the invention to provide a shirt cutting jig that is well suited for use by not-for-profit organizations interested in recycling t-shirts and other textiles in light of the machine's affordability and ease of use.

To achieve the foregoing and other objects, the present invention in accordance with certain embodiments of the present invention, entails a process for converting a textile into yarn using a jig with a base, a clamping bar, a comb-shaped clamping panel, and a cutting fence, along with other components, mounting a tubular body of a textile flat on the top surface of the jig's base, and securing to the base the clamping bar over a first folded edge of the tubular body, securing to the base the clamping panel over a second folded edge of the tubular body. While securing the clamping panel, the clamping panel is positioned over the tubular body so that teeth that extend from the clamping panel extend over the tubular body's second folded edge thus allowing portions of the tubular body's second folded edge to be accessible via the gaps that exist between the teeth. Then, the cutting fence is mounted from the clamping bar to the clamping panel at a first position, and the cutting fence is used as a cutting guide to cut a strip of material of the tubular body using an appropriate cutting tool. The cut strip of material extends from the second folded edge of the tubular body to a position adjacent to but not extending fully to the first folded edge. The cutting fence is repositioned on the jig by mounting the cutting fence to a position that is adjacent to its prior position, and the cutting and repositioning steps are repeated multiple times until all or nearly all (or a substantial portion) of the tubular body is cut into multiple strips of material. The tubular body with the multiple strips of material then is removed from the jig. The tubular body is opened at its first folded edge, and each of the strips of material is cut in a diagonal pattern at the first folded edge to produce a single strip of material. The single strip of material then is converted into a single strip of yarn.

As an aspect of the invention, the clamping bar is secured to the base by moving it from a raised position above the base to a lowered position that is adjacent to the base, and the tubular body is secured to the base by pins that extend downwardly from the clamping bar.

As a feature of this aspect, the base includes a stop bar and the tubular body is initially positioned so that its first folded edge is immediately adjacent to the stop bar of the base. In such position, the first folded edge is disposed immediately beneath the clamping bar and is secured when the clamping bar is moved to the lowered position.

As another aspect of the invention, the clamping panel, prior to be being secured to the base, may be moved along the base to a position on the base suitable to accommodate the particular size of the tubular body being worked.

As a further aspect of the invention, the clamping panel includes a set of pins that extend downwardly at the ends of the clamping panel's teeth, and the pins at the ends of the teeth secure the second folded edge of the tubular body to the base when the clamping panel is secured to the base.

As an additional aspect of the invention, first and second ends of the cutting fence are respectively mounted on the clamping bar and a support bar that is positioned on the base opposite the clamping bar.

As yet another aspect of the invention, the tubular body is produced from a shirt with its sleeves removed.

In accordance with an apparatus embodiment of the invention, a jig for converting a textile into yarn comprises a base, support bar, clamping bar, clamping panel, and cutting fence, in which the support bar includes mounting apertures and is secured to a top of the base, and the clamping bar also includes mounting apertures and is secured to the base. The clamping bar is configured to secure a first folded edge of the tubular body to the base. The clamping panel is configured to be secured to the base and includes a set of teeth to secure a second folded edge of the tubular body to the base. The cutting fence is mountable on and extends between the support bar and the clamping bar using the mounting apertures. The cutting fence is movable along the support bar and the clamping bar using different mounting apertures and enables a user of the jig to cut the tubular body mounted on the base into a body having multiple strips of material that is designed/configured to be converted into usable yarn.

As an aspect of this embodiment, the clamping bar includes a set of pins that extend downwardly towards the base and configured to secure the first folded edge of the tubular body to the base.

As a feature of this aspect, the base includes a stop bar, and the clamping bar is configured to be secured to the stop bar of the base. The pins of the clamping bar are positioned adjacent to the stop bar when the clamping bar is secured to the stop bar.

As another aspect of the invention, the clamping panel is configured to be movable along and secured to the base at a selectable position to accommodate a tubular body of different sizes.

As a further aspect of the invention, the teeth of the clamping panel include downwardly extending pins configured to securely hold the second folded edge of the tubular body to the base when the clamping panel is secured to the base.

As an additional aspect of the invention, apertures between the teeth of the clamping panel are sized to allow a cutting tool to be used to cut the tubular body completely to an end of the second folded edge.

As yet another aspect of the invention, the cutting fence includes first and second mounting ends and a center body disposed between the first and second mounting end, and each of the first and second mounting ends include a respective pin that is configured to be placed within a respective mounting aperture of the support bar and the clamping bar.

As a feature of this aspect, the mounting apertures of the support bar and the clamping bar are spaced along the support bar and the clamping bar, respectively, at equal intervals, and the cutting fence is configured to allow the pins of the first and second mounting ends to be placed within corresponding, respective mountings apertures of the support bar and the clamping bar.

These and other objects, embodiments, aspects and features of the invention are further discussed in the detailed description below.

BRIEF DESCRIPTION OF THE DRAWINGS

The following detailed description, given by way of example and not intended to limit the present invention solely thereto, will best be appreciated in conjunction with the accompanying drawings, wherein like reference numerals denote like elements and parts, in which.

DETAILED DESCRIPTION OF INVENTION

There are numerous ways to recycle used textiles. The present invention is directed to recycling a type of clothing that is worn by a large percentage of people around the world, namely T-shirts and the like. Accordingly, the present invention is directed to a shirt cutting jig and process that converts used (and unworn) T-shirts and similar types of shirts into usable yarn, and does so in a quick, easy and highly cost-efficient manner. As described herein, the jig may be manufactured at relatively low cost and is easily used to cut and transform T-shirts into yarn that in turn can be used to make a wide variety of products, such as rugs, dish cloths, sweaters, hats, and other clothing and non-clothing products.

The term T-shirt is used herein for convenience to refer to both typical T-shirts (also known as "Tee Shirts") and other shirts that have a continuous, tubular-type body. A non-exhaustive list of exemplary shirts that are included with the term "T-shirt" herein are polo shirts, henley shirts, baseball shirts (jerseys), sweatshirts, halter tops, night shirts, etc.

A description of the construction of the shirt cutting jig of the present invention is provided first, followed by a description of the inventive process of using the jig to convert T-shirts into usable yarn.

Shirt Cutting Jig

Figure 1A:
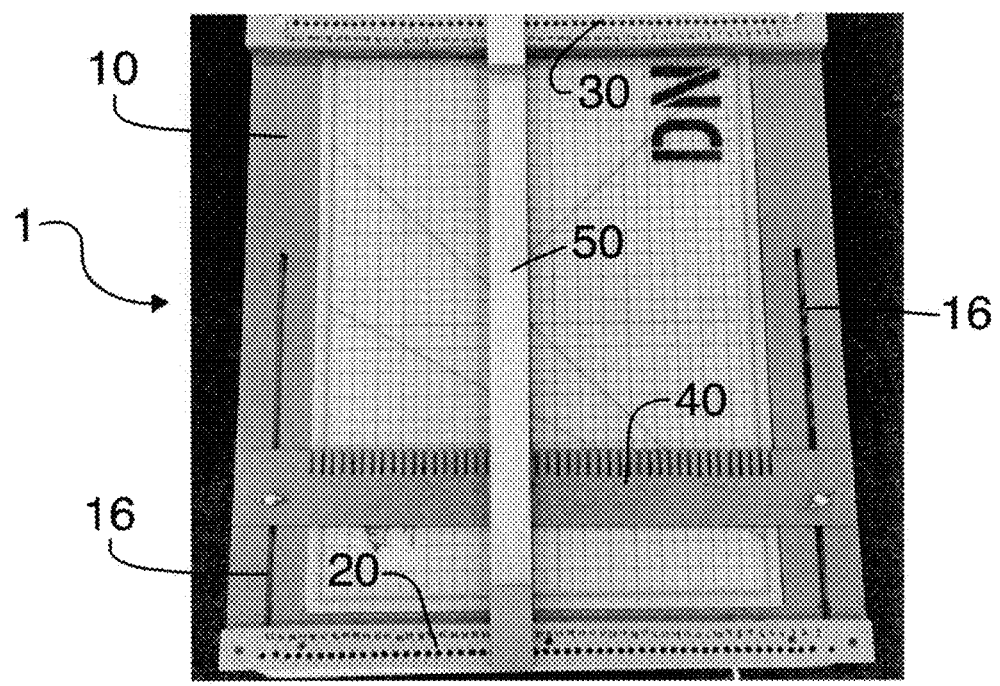
FIGS. 1A and 1B are a photograph and schematic illustration, respectively, of the shirt cutting jig of the present invention.
Figure 1B:
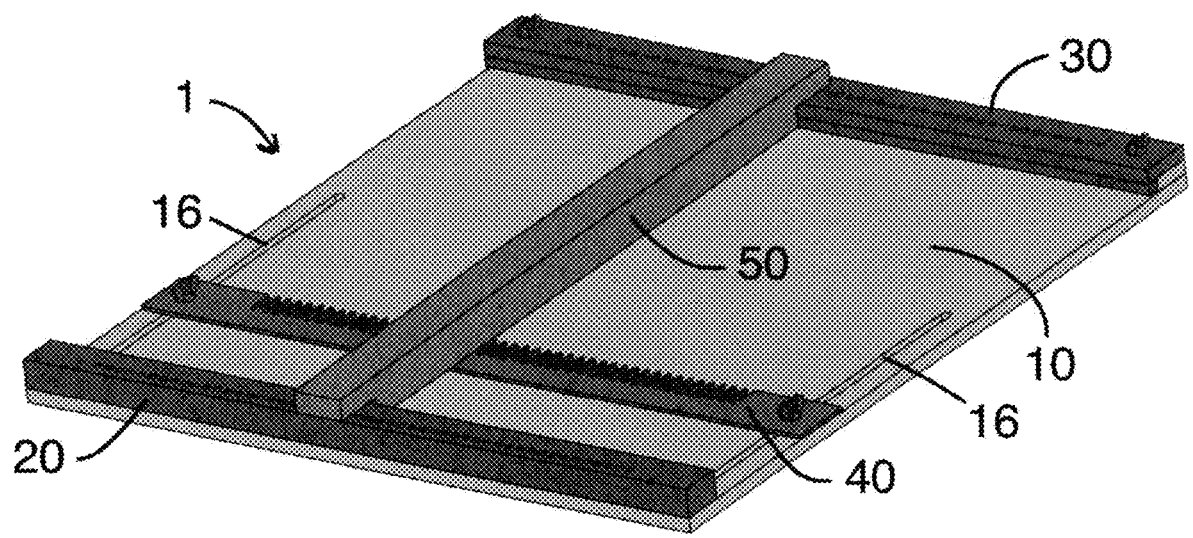

FIGS. 1A and 1B are a photograph and schematic illustration, respectively, of the shirt cutting jig 1 of the present invention (also referred to herein, for convenience, simply as "the jig" or "the machine").

The jig 1 includes several main components, including a base 10, a support bar 20, a clamping bar 30, a clamping panel 40, and a cutting fence 50. Each of these components may be manufactured from different types of materials, such as wood, plastic, metal, or other suitable material.

Base 10

The jig's base 10 supports a shirt during use and enables a user of the jig to cut the shirt in a manner to be described that is then converted into usable yarn. Preferably, base 10 is sufficiently large to hold shirts of different sizes. For example, base 10 may be 100 cm long and 100 cm wide, but a base having other dimensions may be suitably employed. Base 10 should be made of a material sufficiently strong to resist cutting by a cutting tool. Base 10 is shown in FIG. 2A.

Figure 2A:
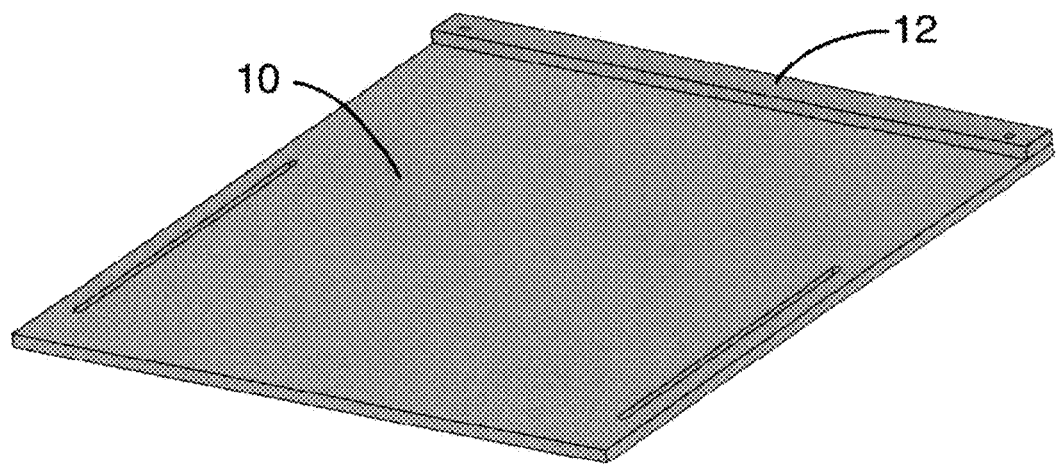
FIG. 2A is a schematic illustration of the shirt cutting jig's base.

As shown in FIG. 2A, base 10 includes a shirt stop bar 12 that operates as a wall/guide for proper placement of an end of a shirt during the herein-described process. The structure/function of shirt stop bar 12 will be further discussed.

Figure 2B:
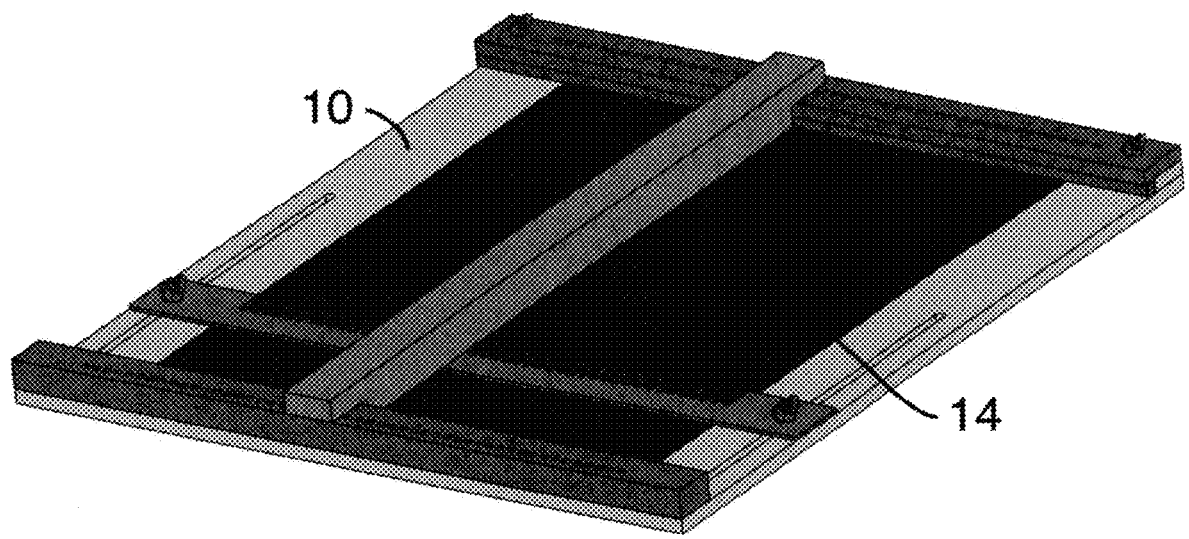
FIG. 2B is a schematic illustration of the shirt cutting jig with a cutting mat embedded within the base.

Base 10 may include an embedded cutting surface. FIG. 2B shows jig 1 with a cutting surface 14 (e.g., a cutting mat) embedded within base 10.

Other features of base 10 are discussed below.

Support Bar 20

Shirt cutting jig 1 of the present invention includes a support bar 20 that is located at one end of the jig as shown in FIGS. 1A and 1B above. Support bar 20 is securely fixed on base 10 and serves as a support for cutting fence 50 in a manner to be described. In FIGS. 1A and 1B above, support bar 20 is shown attached to the front end of base 10. However, the location of support bar 20 may be different than that shown in the figures. For example, support bar 20 may be disposed on another end of base 10 (with other components moved accordingly as would be appreciated from the description herein and by those of ordinary skill in the art).

Support bar 20 is secured to base 10 in any suitable manner. For example, support bar 20 may be secured to base 10 using nuts and bolts, screws, adhesive, or other appropriate technique. In one version, support bar 20 is permanently secured to base 10. In another version, support bar 20 is separable from base 10 to allow the components of the shirt cutting jig to be disassembled for storage or other purpose.

Figure 3A:
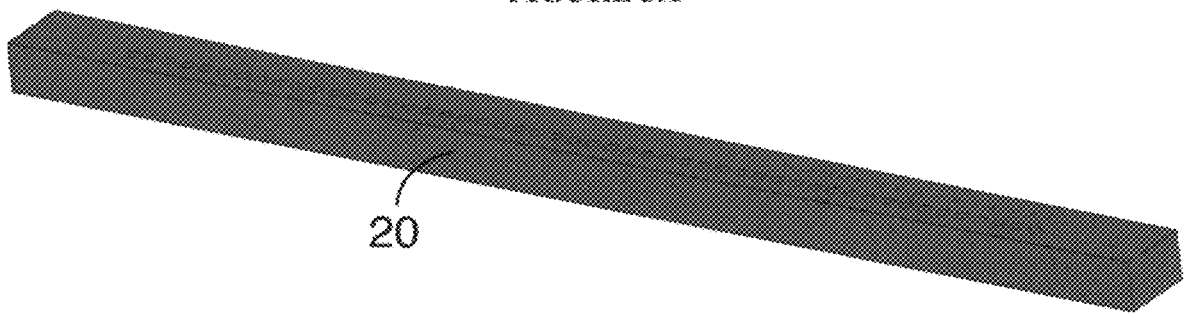
FIG. 3A is a schematic illustration of the shirt cutting jig's support bar.
Figure 3B:
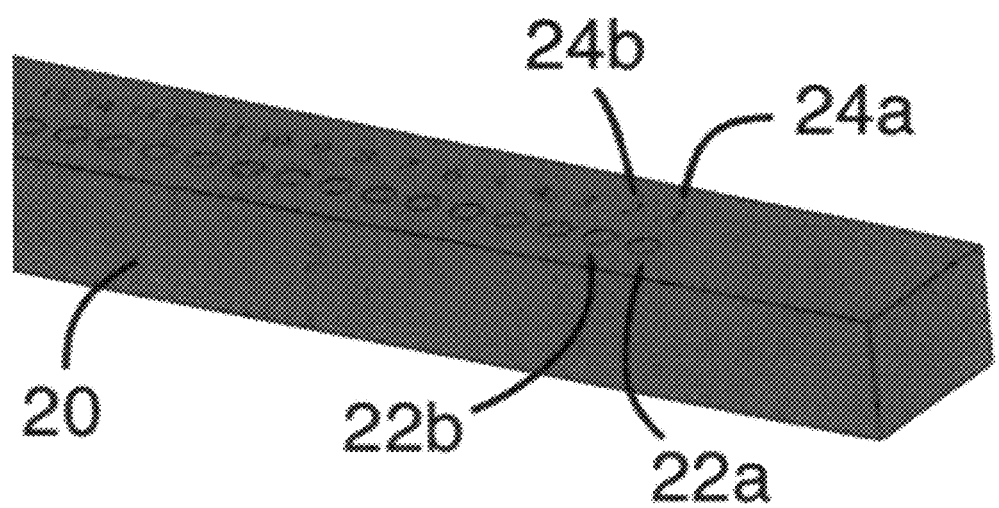
FIG. 3B is an enlarged view of the support bar.

Support bar 20 is shown by itself in FIG. 3A. FIG. 3B is an enlarged view of a portion of support bar 20.

As shown in FIG. 3B, support bar 20 includes a set of mounting apertures 22a, 22b, etc. that are spaced at equal intervals along support bar 20, such as 1 cm apart. In FIG. 3B and various other figures, the apertures are circular in shape. However, the apertures may have a different shape (e.g., oval, rectangular, etc.). Each aperture includes a respective marking 24a, 24b, etc. to allow the apertures to be easily identified during use. In the embodiment of the invention shown in the figures, the markings are numerical, starting with "1" followed by "2," "3," and so on. However, other appropriate markings may be employed, such as letters (e.g., "A", "B", "C", etc.) or symbols. As discussed further below, support bar 20 serves to hold one end of the cutting fence 50 during use.

Clamping Bar 30

Figure 4A:
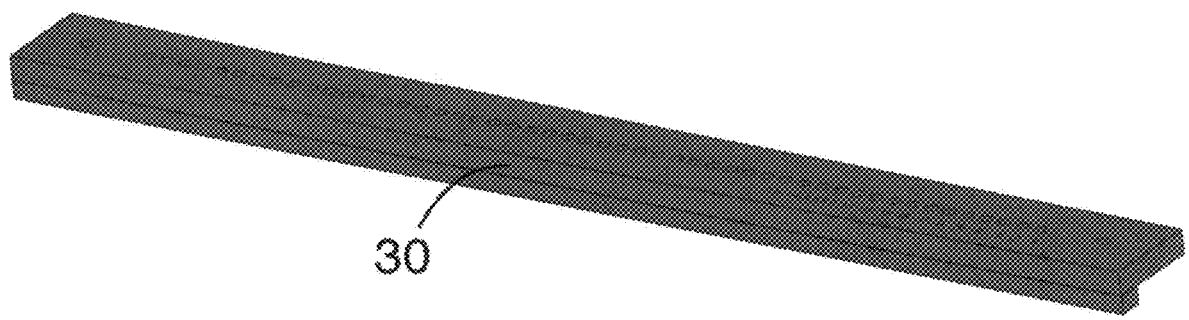
FIG. 4A is a schematic illustration of the shirt cutting jig's clamping bar.

Clamping bar 30 is disposed at the opposite end of base 10 from where support bar 20 is disposed (see FIGS. 1A and 1B). As will be described, clamping bar 30 serves to hold the other end of the cutting fence 50 during use. FIG. 4A shows clamping bar 30 by itself.

As shown in FIG. 4A, clamping bar 30 is L-shaped. Clamping bar 30 may be manufactured from a single piece of material or may be manufactured from multiple components. As shown in FIG. 1B (as well as FIGS. 4C and 4D discussed below), clamping bar 30 is disposed over the base's stop bar 12.

Figure 4B:
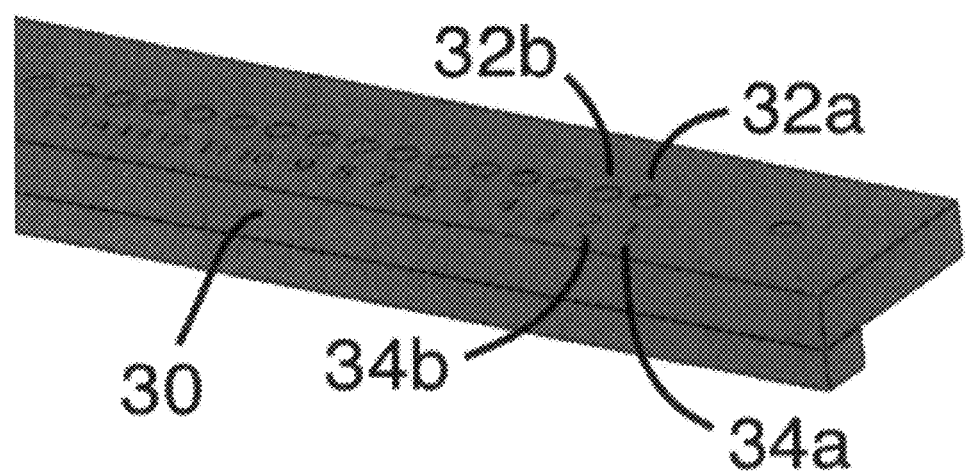
FIG. 4B is an enlarged view of the clamping bar.

Clamping bar 30 includes a set of mounting apertures 32a, 32b, etc. as shown in the enlarged view of FIG. 4B.

In accordance with the present invention, each mounting aperture 32a, 32b, etc. within clamping bar 30 corresponds to and is located opposite to a respective mounting aperture 22a, 22b, etc. within support bar 20. The clamping bar's apertures are spaced at the same distance interval as the support bar's apertures (e.g., 1 cm apart). Similarly, the clamping bar's mounting apertures 32a, 32b, etc. include markings 34a, 34b, etc. that also correspond to the markings 24a, 24b, etc. of the support bar's mounting apertures. As shown in the photograph of an exemplary jig of the present invention in FIG. 1A, both support bar 20 and clamping bar 30 have the same numerical markings (i.e., 1, 2, 3, etc.) for their respective mounting apertures.

Clamping bar 30 is not permanently secured in a fixed manner to base 10. Instead, clamping bar is connected in a manner to allow it to be lifted slightly away from the base to allow a user of the jig to insert an edge of a cut shirt (to be described) between clamping bar 30 and base 10. As will be further described, when clamping bar 30 is in a raised (i.e., lifted) position, one end of the shirt is placed under the clamping bar and positioned so that the shirt end is immediately adjacent to the base's stop bar 12. The clamping bar then is lowered to secure the shirt in place. Stop bar 12 is utilized for alignment purposes and to prevent too much of the shirt from being placed under clamping bar 30.

Figure 4C:
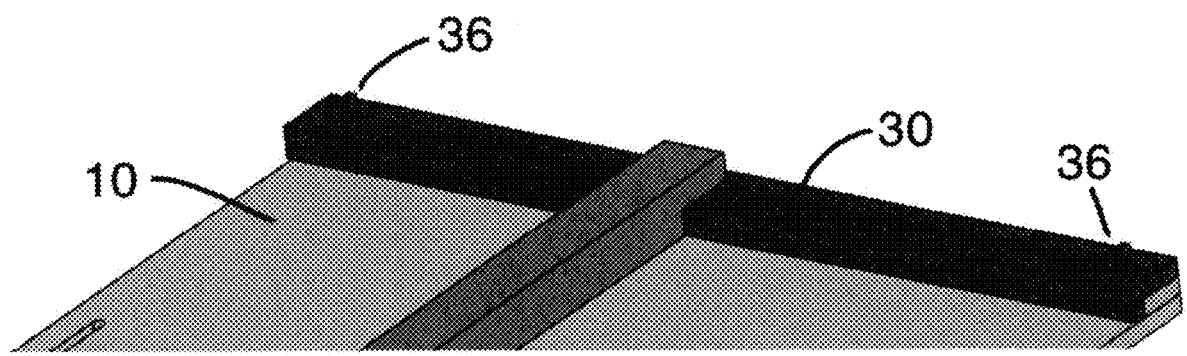
FIG. 4C is another view of the shirt cutting jig showing particularly the clamping bar secured to the base.

Clamping bar 30 is secured to base 10 using a pair of connecting hardware 36. Each connecting hardware 36 is provided near the opposite ends of the clamping bar 30, as shown in FIG. 4C. In the exemplary embodiment shown in the figures, the connecting hardware is comprised of a bolt 36a, wingnut 36b, and spring 36c. As would be appreciated by those of ordinary skill in the art, other types of nuts may be easily employed along with washers, and other hardware can be utilized in place of the bolt/nut type connection technique.

Figure 4D:
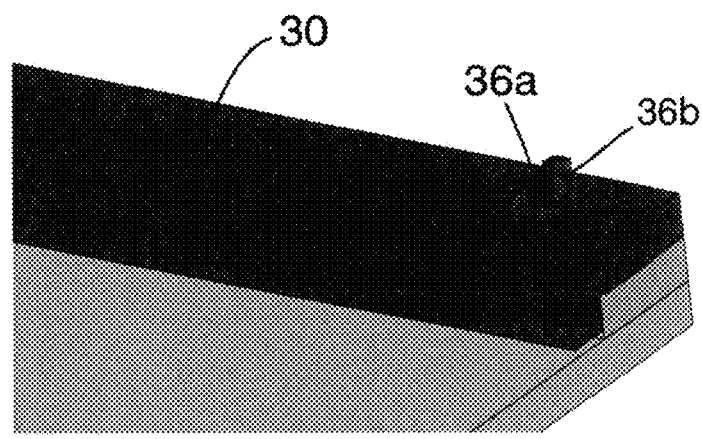
FIG. 4D is an enlarged view of one end of the clamping bar 30 secured to the base.

FIG. 4D is an enlarged view of one end of clamping bar 30, showing the top of a bolt 36a and a wingnut 36b secured to the bolt.

Figure 4E:
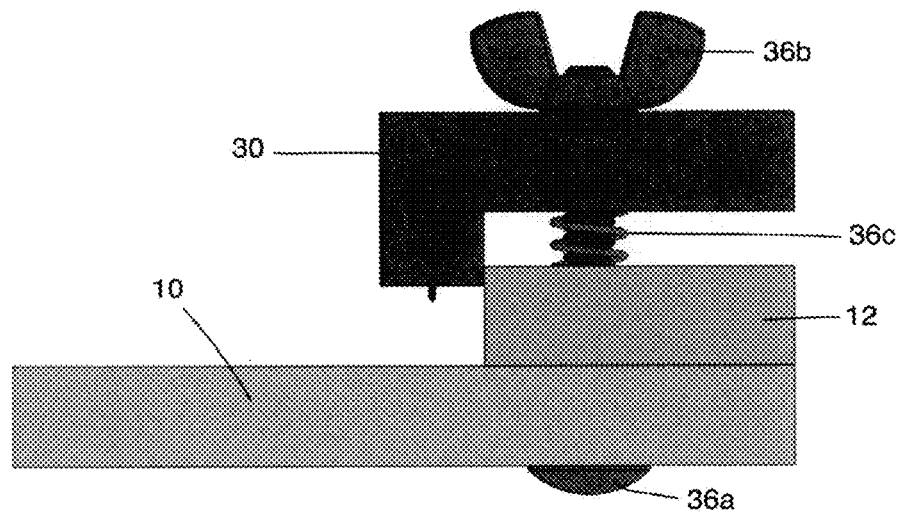
FIG. 4E schematically illustrates the clamping bar from the side and in a loosened state from the base.

FIG. 4E shows the clamping bar 30 from the side and in a loosened state (i.e., lifted or raised state). In this loosened state, an internally disposed spring 36c causes clamping bar 30 to be lifted upwards from the shirt stop bar 12 of base 10. Clamping bar 30 includes an internal recess to accommodate the spring.

As shown in FIGS. 4C, 4D and 4E, bolt 36a extends from the bottom of base 10 and through clamping bar 30, and wingnut 36b is attached to the top of bolt 36a above the clamping bar. Spring 36c is disposed within a recess in clamping bar 30 and extends around bolt 36a. When wingnut 36b is completely tightened, spring 36c is compressed and the bottom surface of clamping bar 30 abuts the top surface of base 10. Conversely, when wingnut 36b of each connecting hardware 36 is loosened, the two springs 36c collectively cause the clamping bar 30 to lift thereby creating a space between clamping bar 30 and base 10. As further discussed below, the end of a shirt is placed in this space.

Figure 4F:
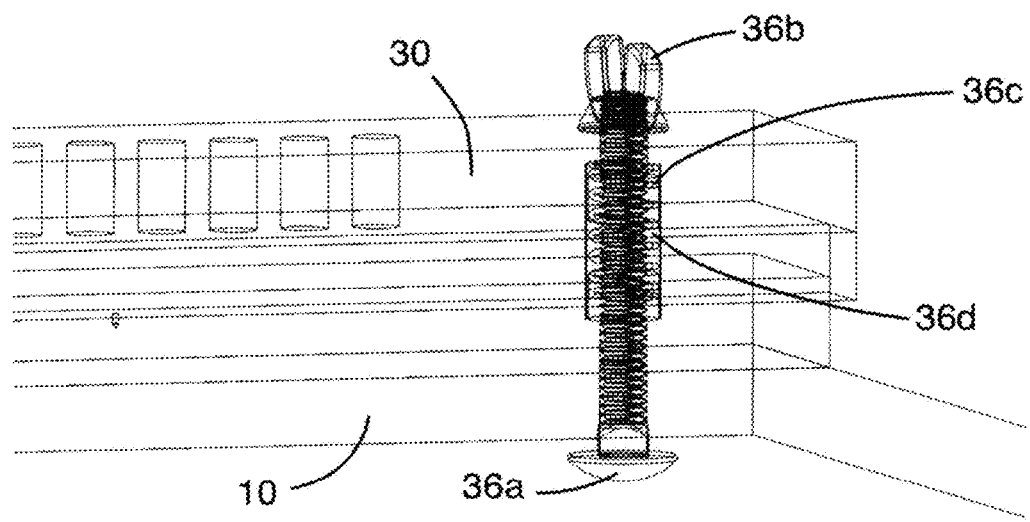
FIG. 4F is a transparent view of the clamping bar secured to the base.

FIG. 4F is a transparent view that shows spring 36c around bolt 36a in a gap 36d within clamping bar 30. It is appreciated that a gap may be disposed within the top of shirt stop 12 to accommodate the spring or a portion of the spring.

As discussed, when the wingnuts are loosened, the springs lift clamping bar 30. When the wingnuts are tightened, the clamping bar 30 comes into contact with base 10, thus securing the end of the shirt that is placed between the clamping bar and the base.

As previously mentioned, other types of connecting hardware may be employed in place of the bolt, nut and spring illustrated in the figures.

Figure 4G:
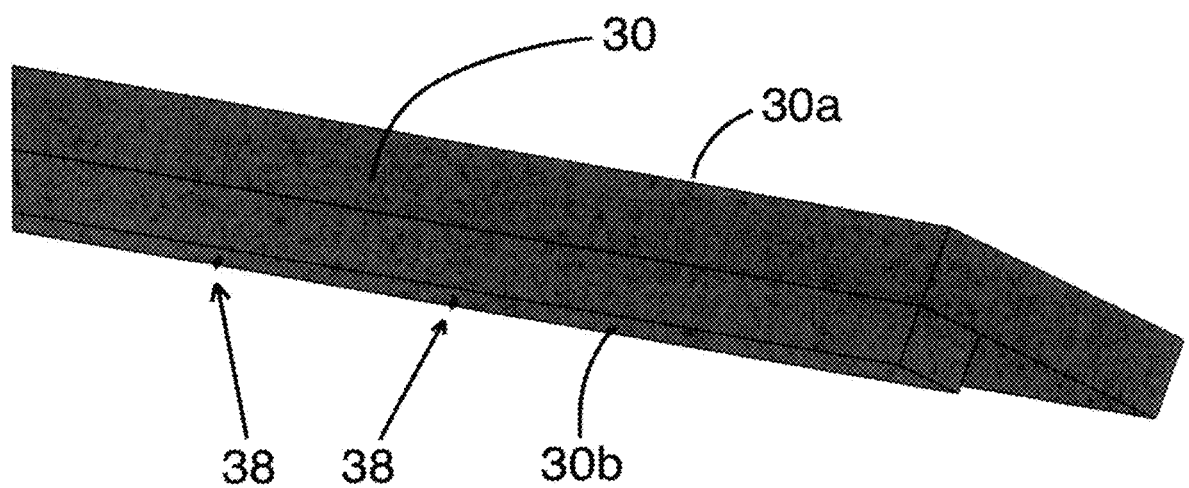
FIG. 4G schematically shows the underside of the clamping bar, to reveal a set of pins that extend downward from the clamping bar's bottom surface.

In accordance with the present invention, clamping bar 30 includes a set of pins that extend from its bottom surface and that serve to securely hold the shirt in place during use of the jig. FIG. 4G shows pins 38 extending downward from the bottom surface 30b of the front portion of clamping bar 30. The top and bottom surfaces of clamping bar 30 are labelled 30a and 30b, respectively.

Clamping bar 30 may include any suitable number of pins 38 spaced along its bottom surface.

Clamping Panel 40 (Clamping Comb 40)

The shirt cutting jig 1 includes a clamping panel 40 that is disposed on base 10 between support bar 20 and clamping bar 30, as shown in FIGS. 1A and 1B and various other figures. Clamping panel 40 is shown by itself in FIG. 5A.

Clamping panel 40 is comb-shaped and includes a set of teeth 44. Clamping panel 40 is also referred to herein as the clamping comb. Clamping panel 40 (clamping comb 40) serves to hold the other side of the shirt during use of the shirt cutting jig of the present invention.

Clamping comb 40 is not permanently fixed to base 10. Instead, and similar to clamping bar 30, clamping comb 40 can be slightly lifted from base 10 (in a loosened state) to allow a small portion of an end of a shirt to be inserted between clamping comb 40 and base 10. During use of the shirt cutting jig, a shirt is placed on base 10 between clamping comb 40 and clamping bar 30. One end of the shirt is secured between clamping comb 40 and base 10. The other end of the shirt is secured between clamping bar 30 and base 10.

Figure 5A:
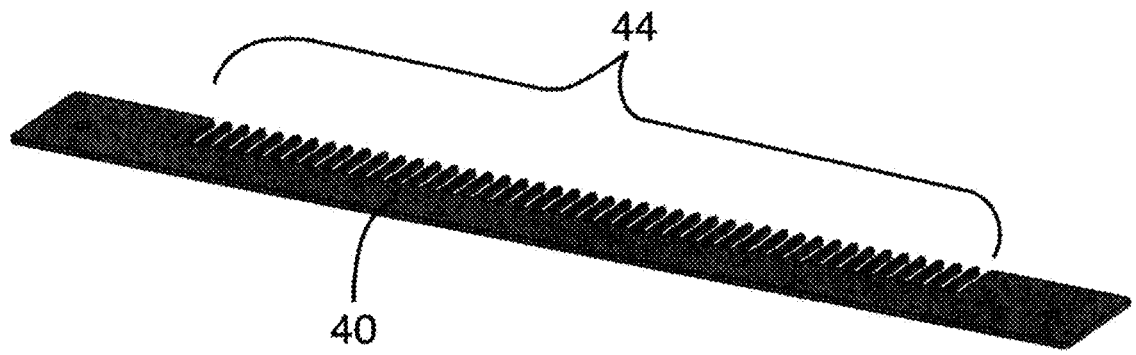
FIG. 5A is a schematic illustration of the shirt cutting jig's clamping panel.
Figure 5B:
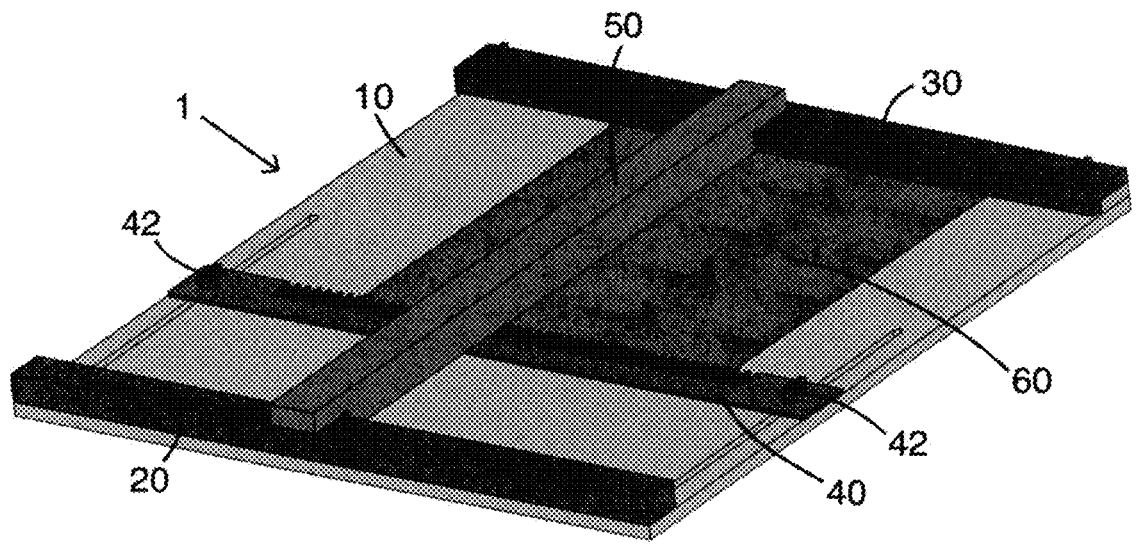
FIG. 5B schematically shows the shirt cutting jig with a shirt mounted thereon.

FIG. 5B is an illustration of the location of a shirt 60 on shirt cutting jig 1. As discussed further below in connection with the described process for converting shirts into yarn, shirt 60 that is mounted on the jig is the tubular portion of the shirt with the top portion removed.

Figure 5C:
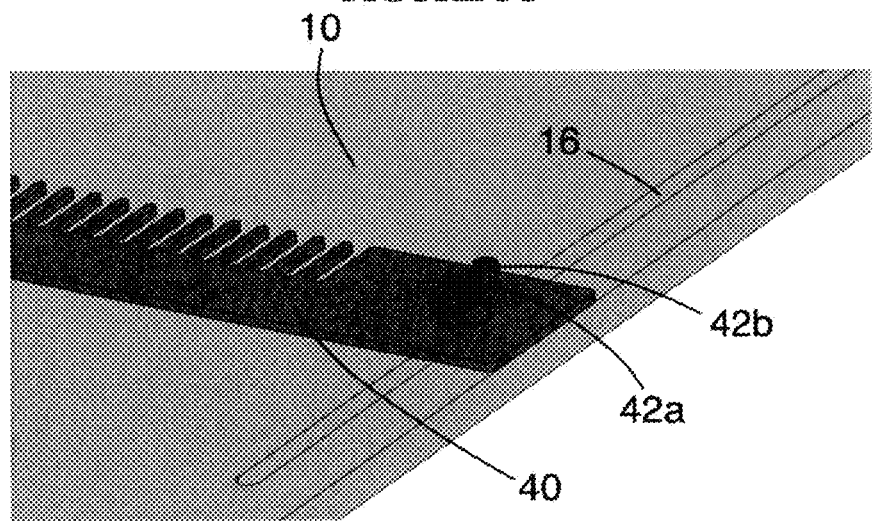
FIG. 5C is an enlarged view of one end of the clamping comb mounted on the base.

Clamping comb 40 includes suitable connecting hardware 42 to allow a user to firmly secure the clamping comb 40 to base 10. The connecting hardware 42 may be a bolt/wingnut combination (similar to the connecting hardware of clamping bar 30). FIG. 5C is an enlarged view and shows one end of clamping comb 40 (disposed on top of base 10). A bolt 42a extends through base 10 and clamping comb 40, and a wingnut 42b is secured to the top of bolt 42a to secure the clamping comb to base 10.

The other end of clamping comb 40 likewise includes suitable connecting hardware, such as a bolt/wingnut combination, to secure the other end of the clamping comb to the base.

Figure 5D:
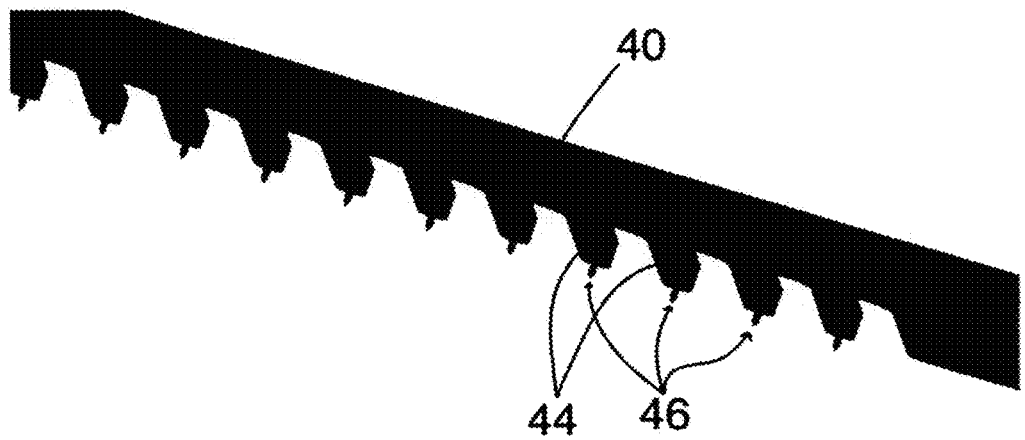
FIG. 5D schematically shows the underside of the clamping comb, revealing a set of pins that extend from the underside of the clamping comb's teeth.

As shown in FIGS. 5A, 5B and 5C, clamping comb 40 includes a set of teeth 44. FIG. 5D shows the underside of clamping comb 40. As shown in FIG. 5D, the clamping comb includes a set of pins 46, with a respective pin extending from the underside of each tooth 44.

Figure 5E:
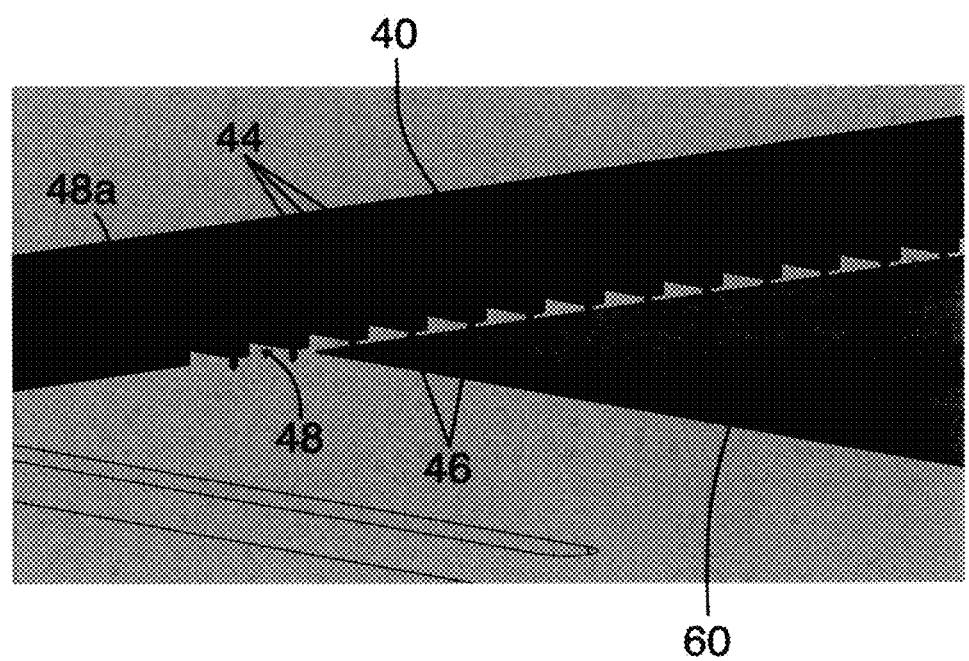
FIGS. 5E, 5F and 5G are used to describe the proper position of a shirt when securely held to the base by the clamping comb.

During use of the jig, one end of the shirt is placed under the edges of the clamping comb's teeth 44, and when the clamping comb 40 is secured to base 10, the pins 46 push against (i.e., dig into) the fabric of the shirt to securely hold it in place. FIG. 5E shows clamping comb 40 in a slightly raised position over base 10 with an edge of shirt 60 placed beneath the teeth.

As illustrated in FIG. 5E, the pins 46 come into contact with the shirt as clamping comb 40 is lowered, and the pins then securely hold the shirt when the clamping comb is fully lowered and secured to base 10.

Figure 5F:
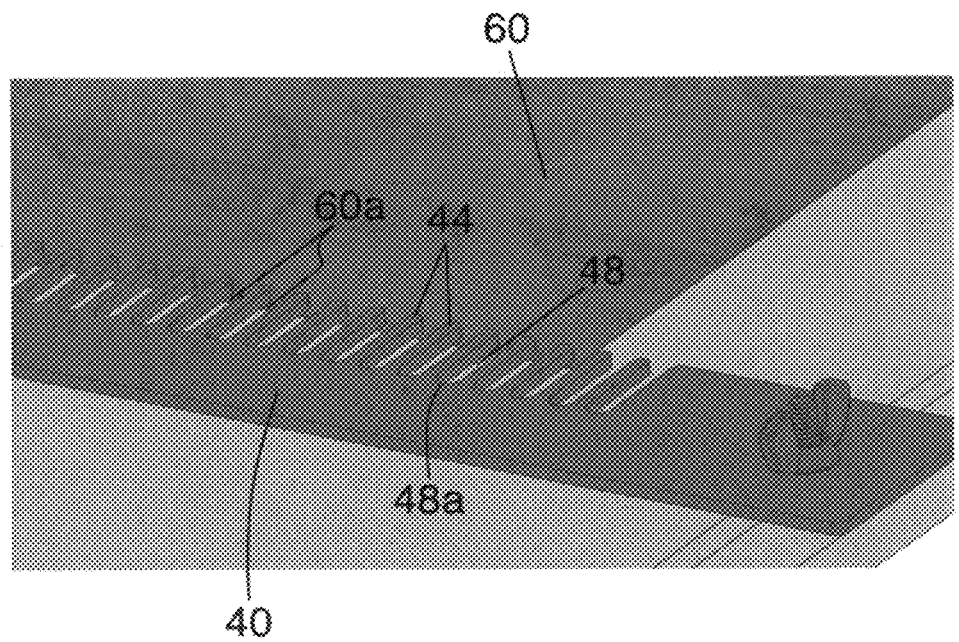
Figure 5G:
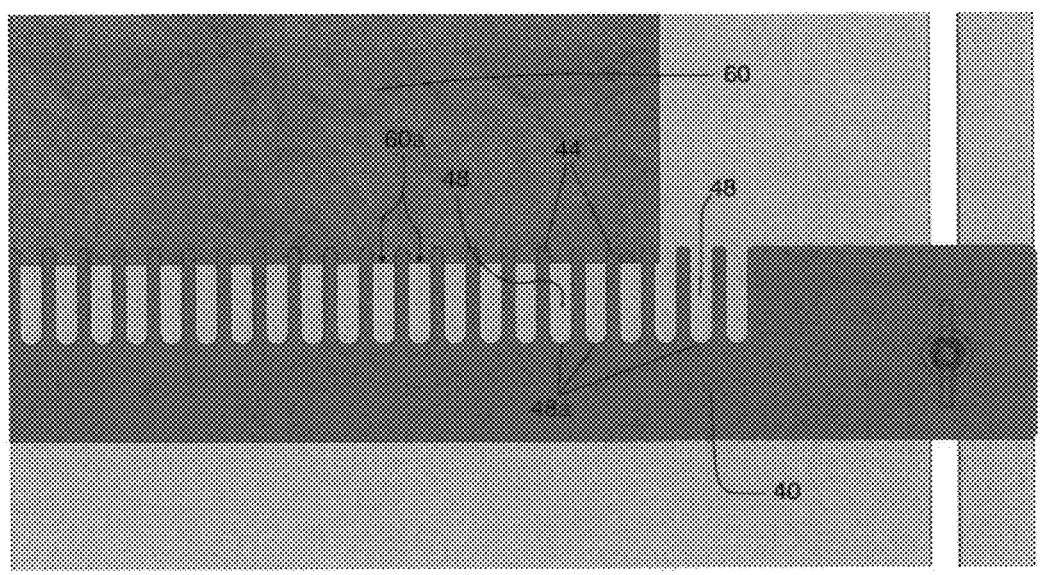

During use of the jig, the edge of shirt 60 should be properly positioned beneath clamping comb 40. FIGS. 5F and 5G show the proper position of the shirt's edge 60a beneath clamping comb 40. As shown, the shirt edge 60a is disposed near the end of each of the clamping comb's teeth 44, but still under the pins 46 (of the teeth) so that the shirt is secured by the pins when the clamping comb 40 is fully secured to the jig's base. As shown in FIGS. 5F and 5G, a gap exists between the shirt edge 60a and the ends 48a of each of the apertures 48 that exist between the teeth 44.

As will be further described, to facilitate proper cutting of the shirt, the edge of the shirt held under clamping comb 40 must be accessible by a cutting tool. The apertures 48 between the teeth 44 of the clamping comb serve as initial starting positions for the cutting tool when the shirt is cut into strips (to be described). Apertures 48 between the teeth of the clamping comb are referred to herein as the cutting apertures.

The cutting apertures 48 extend along the clamping comb at the precisely same distance (e.g., 1 cm apart) as the mounting apertures within support bar 20 and clamping bar 30. During use of the shirt cutting jig, the movable cutting fence 50 (described further below) employs the mounting apertures for positioning purposes, and the movable cutting fence is moved along the mounting apertures during the herein described process. As further described, cutting fence 50 serves as a cutting guide (i.e., a straight edge) for a cutting tool during use of the jig of the present invention. When cutting fence 50 is mounted at each cutting position, there exists a respective cutting aperture 48 of clamping comb 40 that is appropriately positioned adjacent to the cutting fence. Accordingly, regardless of where cutting fence 50 is mounted (i.e., regardless of the particular mounting apertures of support bar 20 and clamping bar 30 within which cutting fence 50 are mounted), clamping comb 40 provides a suitable cutting aperture 48 adjacent the cutting fence. These features will be further appreciated in connection with the below-described process.

Clamping comb 40 is relatively thin (e.g., 0.2 cm or 0.3 cm thick) as compared to the thicknesses of the other main components, as shown in FIG. 5B above and various other figures. With such thin dimension, cutting fence 50 when installed on the jig functions properly as a cutting guide for the cutting tool during use of the jig of the present invention. More particularly, and as illustrated in FIG. 5B, the gap (if any) between cutting fence 50 and the shirt 60 mounted on the jig is sufficiently small to enable cutting fence 50 to be effectively used as a cutting guide as strips of the shirt are cut as further described.

Clamping comb 40 is movable along base 10 to accommodate shirts of different sizes. As shown in FIGS. 1A and 1B, base 10 includes a pair of slots 16. The close-up view of FIG. 5C above shows one end of clamping comb 40 and a portion of one of the slots 16.

The connecting hardware 42 of the clamping comb 40 employ both slots 16 to facilitate movement along base 10. As shown in FIG. 5C, bolt 42a extends from the bottom of base 10, through slot 16, and through clamping comb 40, and wingnut 42b is attached to the top of bolt 42a. Accordingly, when the bolts 42a on both sides of the clamping comb are loosened, the clamping comb easily slides along base 10 (via the slots 16).

As further discussed below, clamping comb 40 is properly positioned along base 10 to accommodate the particular size of the shirt to be cut by the shirt cutting jig. Therefore, shirts of different sizes may be used by the jig. Clamping comb 40 is moved closer to clamping bar 30 to accommodate smaller shirts. Clamping comb 40 is moved further away from clamping bar 30 to accommodate larger shirts.

Figure 6A:
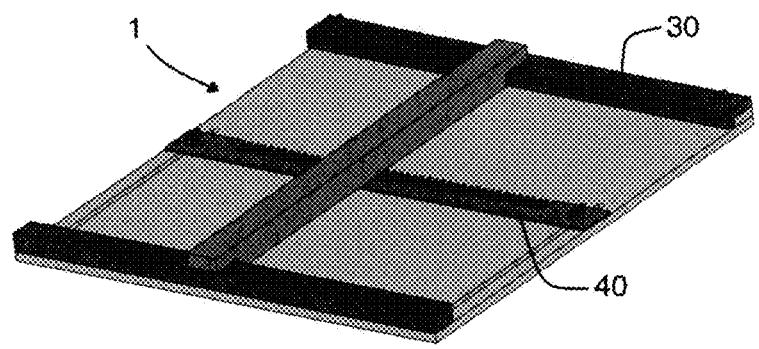
FIGS. 6A and 6B schematically illustrate clamping bar 30 in different positions within the shirt cutting jig.
Figure 6B:
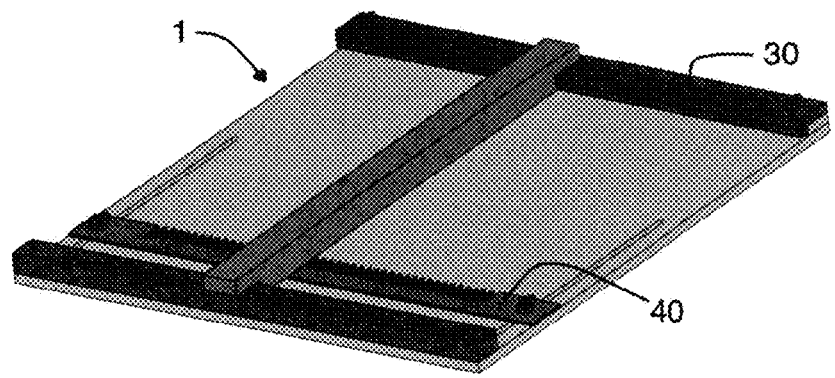

FIG. 6A shows the shirt cutting jig 1 with clamping comb 40 relatively close to clamping bar 30, and FIG. 6B shows the shirt cutting jig 1 with clamping comb 40 further away from clamping bar 30.

It is appreciated that the connecting hardware of clamping comb 40 may be different than that shown in the figures. Moreover, the manner of allowing clamping comb 40 to be moved closer to or further away from clamping bar 30 may be different than that described herein.

Movable Cutting Fence 50

Figure 7A:
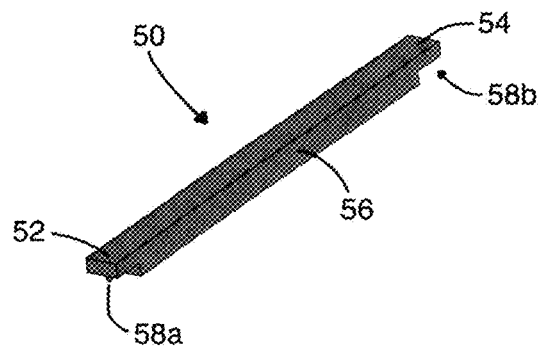
FIGS. 7A and 7B are different views of the shirt cutting jig's movable cutting fence.
Figure 7B:
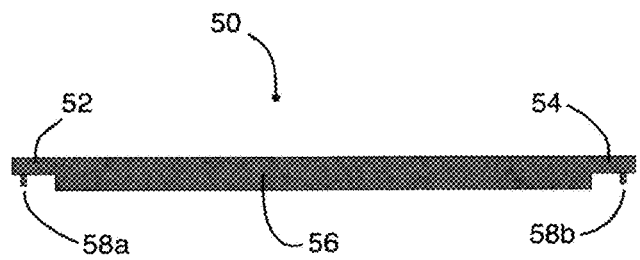

Movable cutting fence 50 is shown within the jig in FIGS. 1A and 1B and various other figures. Movable cutting fence 50 is shown by itself in FIGS. 7A (perspective view) and 7B (side view). For convenience, movable cutting fence 50 also is sometimes referred to herein as the "cutting fence" or "fence."

Fence 50 is T-shaped and includes three sections: mounting ends 52 and 54, and a center body 56. Each mounting end includes a respective protruding pin 58a, 58b that serve to hold fence 50 in place when mounted on support bar 20 and clamping bar 30.

Figure 7C:
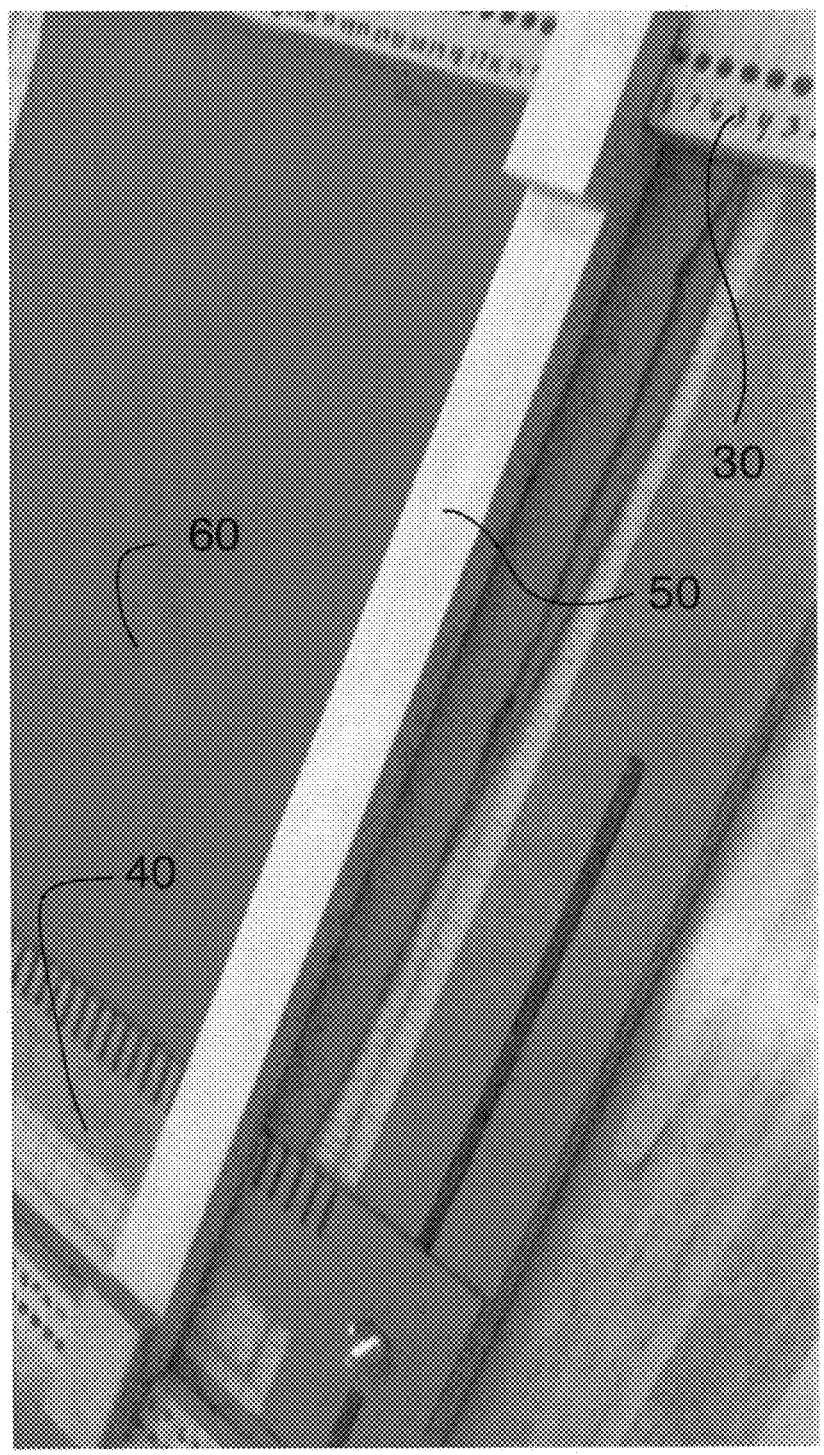
FIG. 7C shows an appropriate starting position of the movable cutting fence on the shirt cutting jig prior to cutting the shirt using the described process.

During use of the jig, and after a shirt is properly secured on the jig's base, fence 50 is initially mounted at an appropriate starting position to begin cutting the shirt as further described herein. For instance, an appropriate starting position is to place the fence 50 near the right end of shirt 60, such as shown in FIG. 7C.

To secure fence 50 to the jig, the fence's pins 58a and 58b are placed within respective mounting apertures of support bar 20 and clamping bar 30. That is, pin 58a (on mounting end 52 of fence 50) is placed within a suitable mounting aperture of support bar 20 and, at the same time, pin 58b (on mounting end 54 of fence 50) is placed within the corresponding mounting aperture (with the same marking) of clamping bar 30.

After fence 50 is properly positioned, the user of the jig utilizes a cutting tool to cut a single strip of the shirt. Fence 50 then is lifted and repositioned into an adjacent set of mounting apertures of support bar 20 and clamping bar 30. For example, if the fence's pins are placed within the mounting apertures with the marking "5," then after a strip is cut, the fence is repositioned into the mounting apertures marked with a "6" and another strip is cut. This process is repeated, as further explained in the process described below.

Process for Converting Shirts into Yarn

Having described the structure of the shirt cutting jig of the present invention, T-shirts may be quickly converted into usable yarn by the herein described inventive process.

Figure 8A:
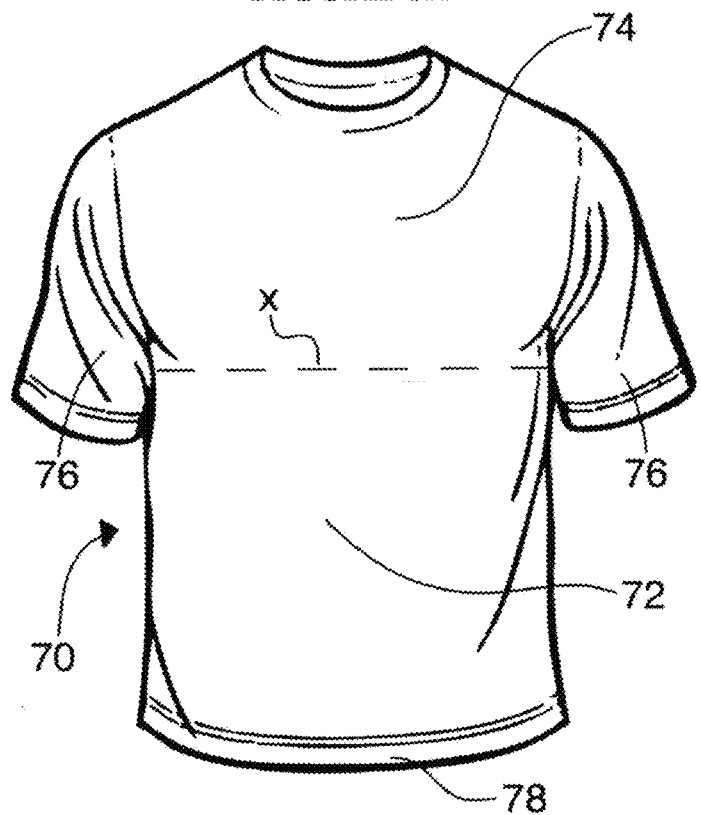
FIG. 8A is a schematic illustration of a standard T-shirt that may be used by the inventive shirt cutting jig.

As mentioned above, different types of shirts may be employed with the present invention. Ideally, the shirts have a continuous, tubular-type body. FIG. 8A is a schematic illustration of a standard T-shirt 70 that contains a tubular body.

Figure 8B:
FIG. 8B shows an exemplary rotary cutter that may be employed to cut the shirt in accordance with the described process.

T-shirt 70 shown in FIG. 8A includes a tubular lower portion 72 and a top portion 74. The sleeves 76 extend from the top portion 74. Initially, the top portion 74 is removed from the T-shirt 70 using any suitable tool, such as a pair of scissors, a rotary cutter or other appropriate cutting utensil. In general, a sharp rotary cutter, such as shown in FIG. 8B, will be able to quickly cut the T-shirt as needed when placed on a suitable cutting surface.

Figure 9:
FIG. 9 illustrates cutting a T-shirt using a rotary cutter.

Preferably, the T-shirt is cut immediately below the sleeves 76 (e.g., along line "x" shown in FIG. 8A) to maximize the size of the remaining tubular lower portion 72. FIG. 9 illustrates how the T-shirt may be cut using a rotary cutter.

If the lower edge 78 of the T-shirt (shown in FIG. 8A) is reinforced or otherwise inappropriate to convert into yarn, the lower edge 78 can be removed.

The tubular lower portion 72 of the shirt is converted into usable yarn using the shirt cutting jig of the present invention. The tubular lower portion of the shirt is sometimes referred to herein, for convenience, as the tubular body or, more simply, the shirt (with it understood that the top portion has been cut off before use of the shirt cutting jig).

Initially, and before the shirt is mounted on jig 1 of the present invention, the cutting fence 50 is removed from the jig, and both clamping bar 30 and clamping comb 40 are loosened. Clamping comb 40 then is moved relatively close to support bar 20 to provide a space to mount the shirt.

Figure 10A:
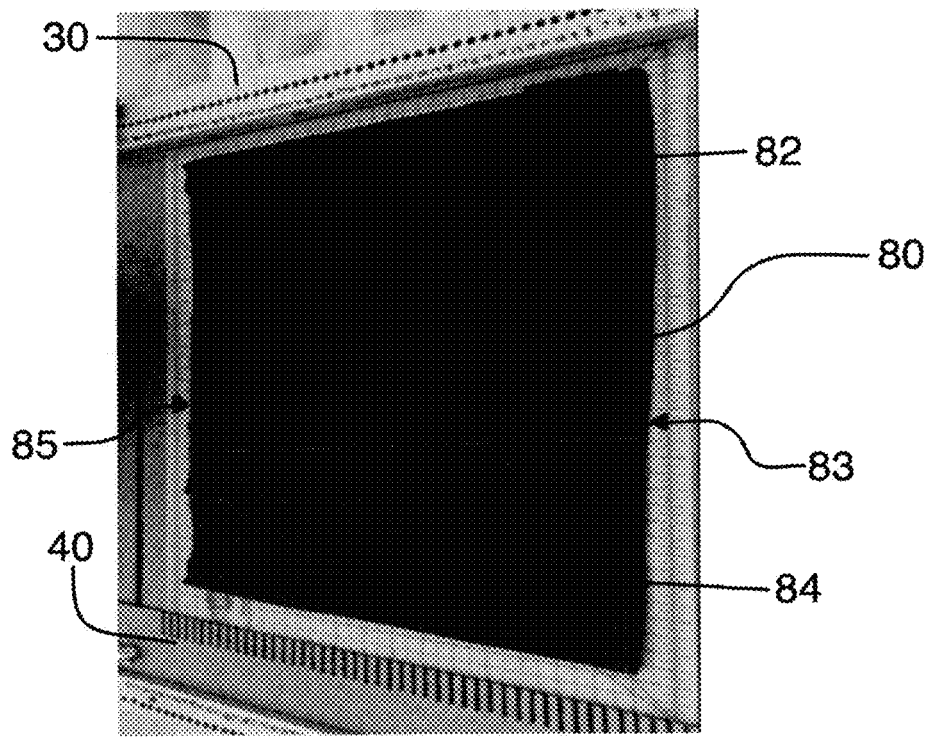
FIG. 10A shows the initial placement of a shirt on the base of the shirt cutting jig prior to securing the shirt to the shirt cutting jig.

A shirt 80 (i.e., the tubular body) is placed flat on the jig's base 10 as shown in FIG. 10A, with the top and bottom surfaces of the shirt resting on one another. Preferably, the shirt in such position rests on the jig's base as flat as reasonably possible. As shown, one of the shirt's folded edge 82 is placed parallel to clamping bar 30. One open end 83 of the shirt extends along the right edge of the jig. The other folded edge 84 of the shirt extends adjacent to clamping comb 40. Finally, the other open end 85 of the shirt extends along the left edge of the jig.

Shirt 80 is moved/shifted to place folded edge 82 underneath the raised clamping bar 30. Folded edge 82 may be in immediate contact with the base's shirt stop bar 12. As mentioned herein, shirt stop bar 12 prevents too much of the shirt from being positioned underneath clamping bar 30. After the shirt is properly positioned, the clamping bar's connecting hardware 36 (see FIG. 4C) are tightened to secure the shirt's folded edge 82 in place. The clamping bar's pins 38 (see FIG. 4G), which dig into the shirt's edge, assist to secure the shirt's edge 82 in place.

Figure 10B:
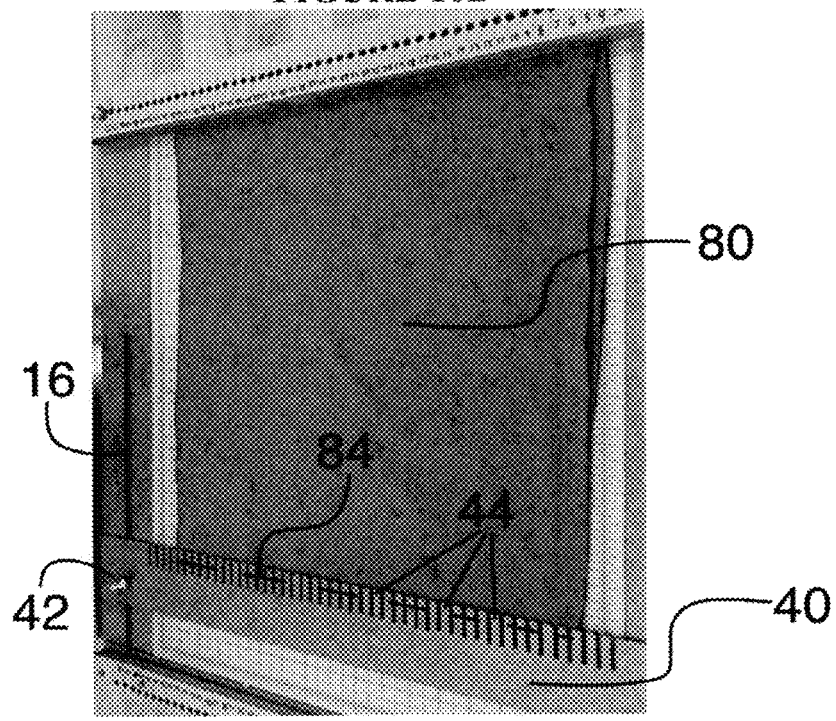
FIG. 10B is used to describe how to secure the shirt to the shirt cutting jig.

Next, clamping comb 40 is moved into proper position so that the ends of its teeth 44 are positioned above the shirt's other folded edge 84, as shown in FIG. 10B (folded edge 84 of the shirt represented by the dashed line in FIG. 10B).

As previously discussed, clamping comb 40 is movable along slots 16 within the base to accommodate shirts of different sizes (see FIGS. 6A and 6B). Clamping comb 40 is properly positioned so that its pins 46 are immediately above the shirt's folded edge 84, as previously explained with reference to FIGS. 5E, 5F and 5G. Importantly, edge 84 of the shirt should be sufficiently far from the closed ends 48*a* of the clamping comb's cutting apertures 48 (see FIG. 5G) to allow the blade of the cutting tool to start beyond the shirt edge's 84.

Preferably, the shirt is resting on base 10 in a relatively flat manner. If not, the user can loosen clamping bar 30 and/or clamping comb 40, reposition the shirt as needed, and then tighten the connecting hardware of clamping bar 30 and clamping comb 40 to secure the shirt in place.

Figure 10C:
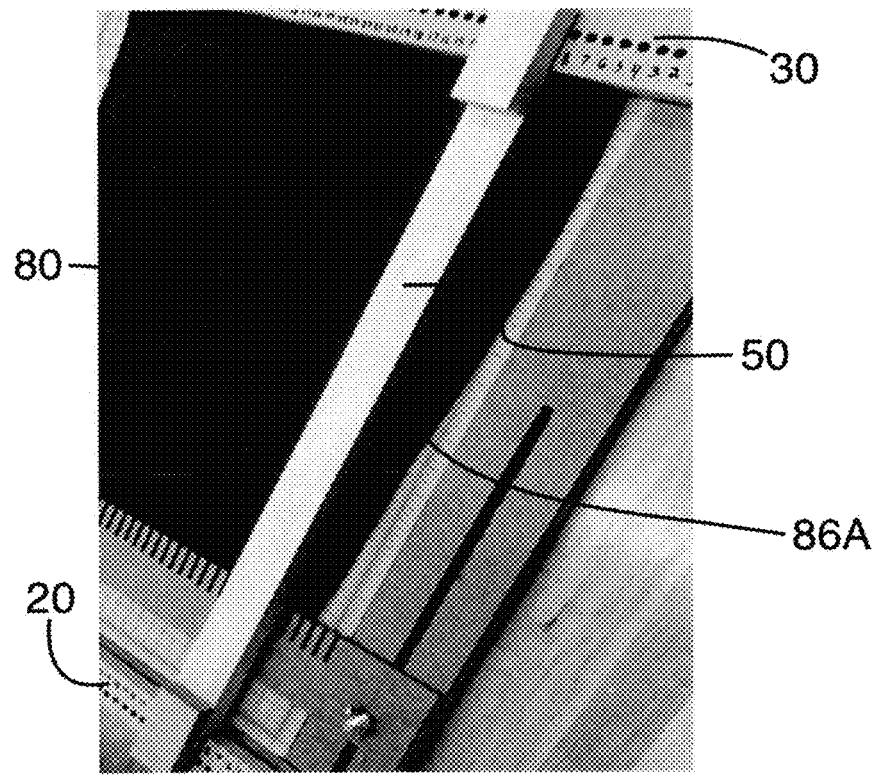
FIG. 10C shows the initial location of the movable cutting fence after the shirt is secured to the shirt cutting jig.

After shirt 80 is in place and fully secured within the jig, cutting fence 50 is positioned at an initial cutting position, as shown in FIG. 10C. As shown, cutting fence 50 is positioned (i.e., installed on support bar 20 and clamping bar 30) so that a small strip of material 86A of shirt 80 is visible and ready to be cut. As discussed above, cutting fence 50 is secured to the jig by placing the fence's pins 58*a* and 58*b* within respective mounting apertures of support bar 20 and clamping bar 30.

Figure 10D:
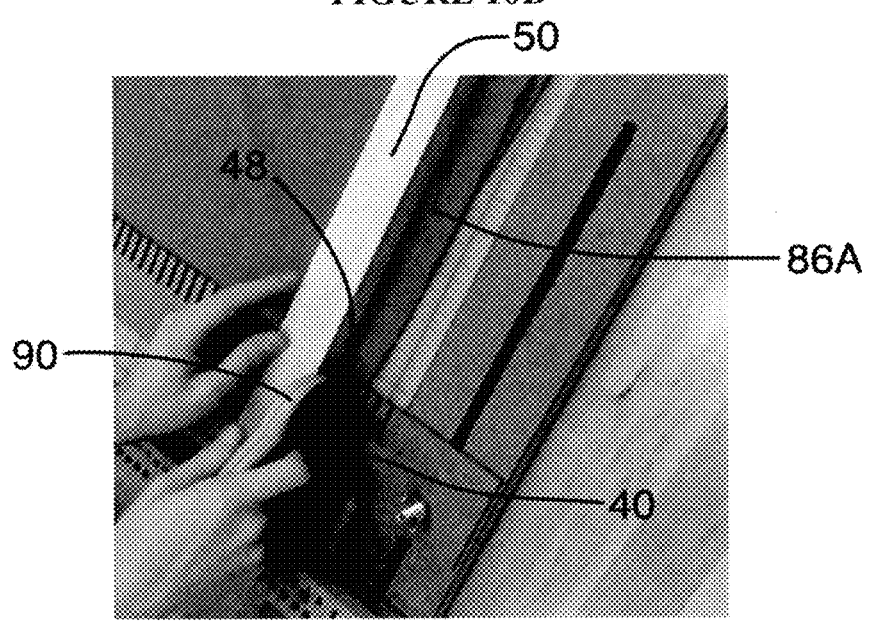
FIGS. 10D, 10E, 10F and 10G are used to describe cutting the first strip in accordance with the present invention.
Figure 10E:
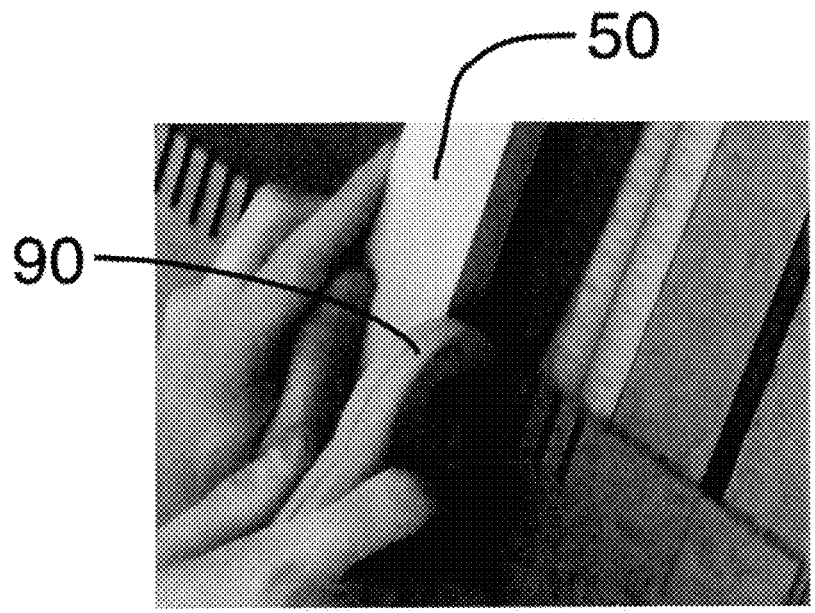

The small strip of material 86A then is cut by placing a cutting roller 90 within the clamping comb's cutting aperture 48 that is immediately adjacent to cutting fence 50, and moving cutting roller 90 along the cutting fence towards clamping bar 30. FIGS. 10D and 10E show the initial placement of cutting roller 90. The user moves the cutting roller from this initial position towards clamping bar 30 to cut the first strip.

Figure 10F:
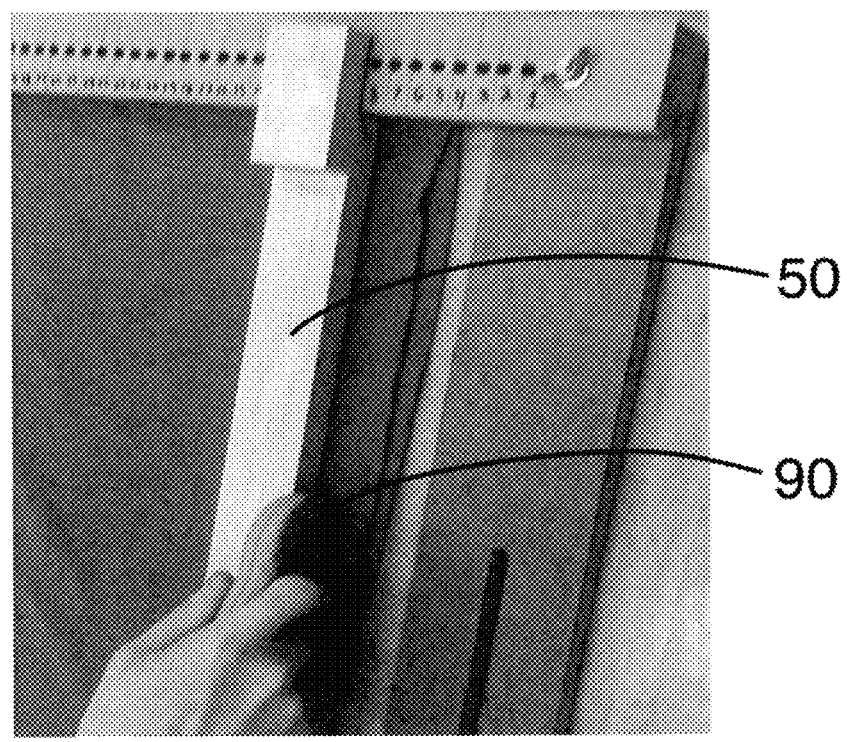

FIG. 10F shows the position of cutting roller 90 about halfway between clamping comb 40 and clamping bar 30.

Figure 10G:
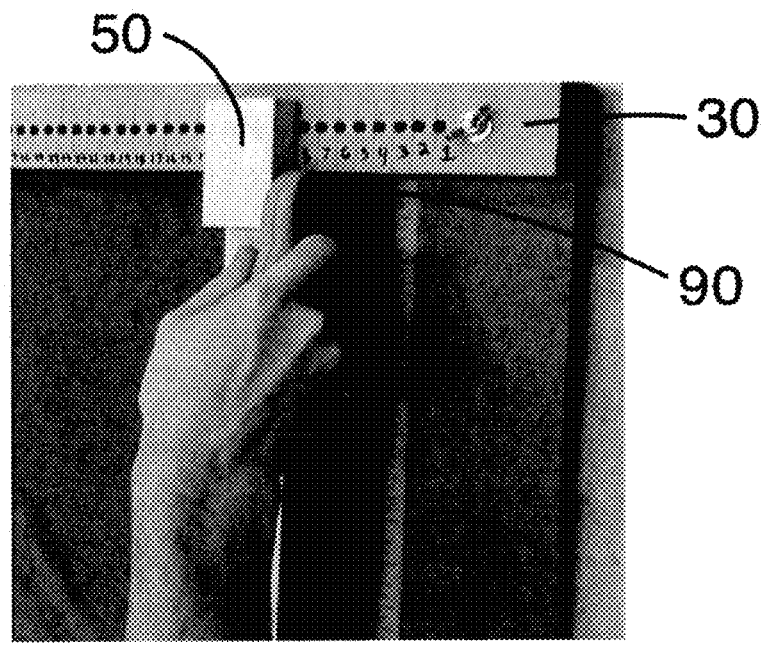

To cut straight or in a near-straight manner, cutting roller 90 is kept immediately adjacent to cutting fence 50 so that cutting fence 50 operates as a straight-edge or guide for the cutting tool. The user continues to move cutting roller 90 until the tool hits clamping bar 30, as shown in FIG. 10G.

At this point, the first cut of the shirt within the jig is complete, and a first strip has now been created. This first strip (as well as all subsequently cut strips) is not fully cut away from the remainder of the shirt, but instead remains connected at the edge 82 of the shirt that is disposed beneath clamping bar 30. However, the cut strip is disconnected at its other end (i.e., shirt edge 84) since the cutting roller is able to cut/move past the shirt edge 84 due to the existence of the cutting apertures 48 of clamping comb 40. More specifically, each cutting aperture is sufficiently long to allow the blade of the cutting roller to initially start on the jig's base at a position where there is no shirt. The cutting roller then proceeds to slide/cut from the very beginning of the shirt edge 84.

However, as previously discussed, the other edge 82 of the shirt is not cut since a small part of that edge is positioned underneath clamping bar 30. Hence, the user is unable to inadvertently or intentionally cut to the very end of the other edge.

Figure 10H:
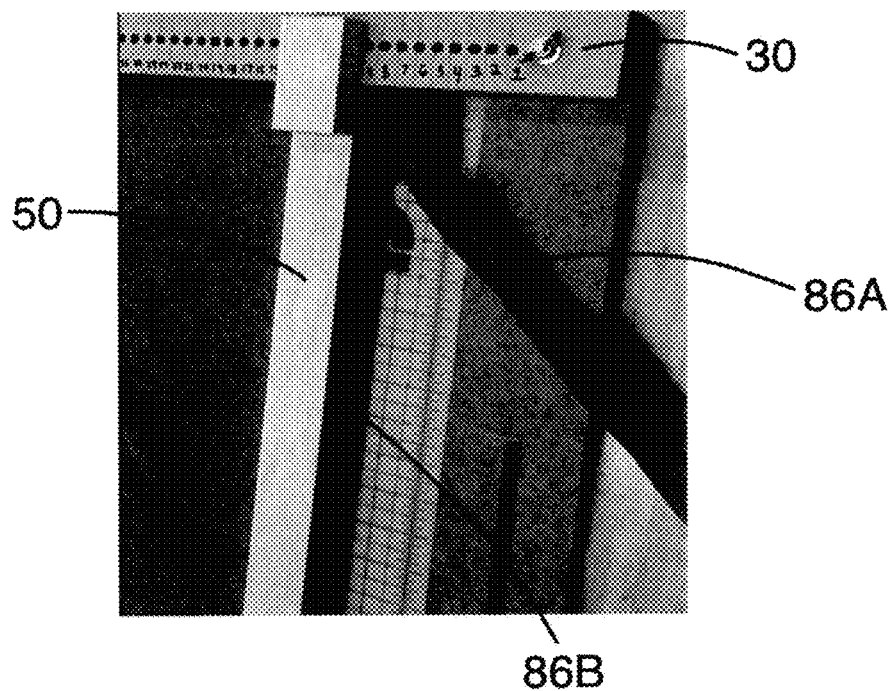
FIG. 10H shows the shirt mounted on the movable cutting fence with a first strip cut.

After the first strip is cut, cutting fence 50 is lifted and repositioned into the next set of mounting apertures of the support bar 20 and clamping bar 30 to expose the second strip 86B to be cut, as shown in FIG. 10H. In FIG. 10H, the first cut strip is labelled 86A, and the second strip (to be cut) is labelled 86B.

Like the initial cut, cutting roller 90 is placed within the cutting aperture 48 of clamping comb 40 that is now immediately adjacent the cutting fence 50, and moved/rolled towards clamping bar 30 (using cutting fence 50 as a guide) to cut the second strip 86B. As previously discussed, since the cutting apertures 48 of clamping comb 40 are aligned with the positions of the mounting apertures of support bar 20 and clamping bar 30, each time cutting fence 50 is repositioned, there always is a respective cutting aperture 48 that is properly positioned immediately adjacent to the cutting fence to enable the user to use the cutting aperture as a starting point to cut a strip of the shirt.

Figure 10I:
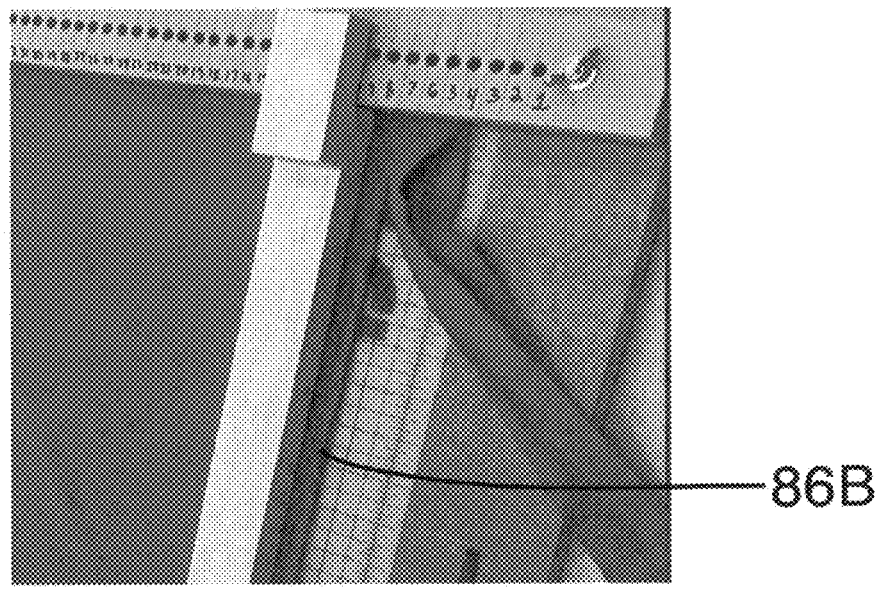
FIG. 10I shows the mounted shirt with a second strip cut.

FIG. 10I shows the completion of cutting the second strip 86B.

The cutting fence 50 is repositioned again (i.e. moved to the next set of mounting apertures in support bar 20 and clamping bar 30) to expose the third strip to be cut. And, again, the user places cutting roller 90 within the cutting aperture 48 of clamping comb 40 that is now immediately adjacent the cutting fence 50, and moves/rolls cutting roller 90 towards clamping bar 30 (again using cutting fence 50 as a guide) to cut the third strip.

These steps (i.e., moving the cutting fence and then cutting a strip) are repeated until all or nearly all the entire shirt 80 has been cut into multiple strips of material.

Figure 11A:
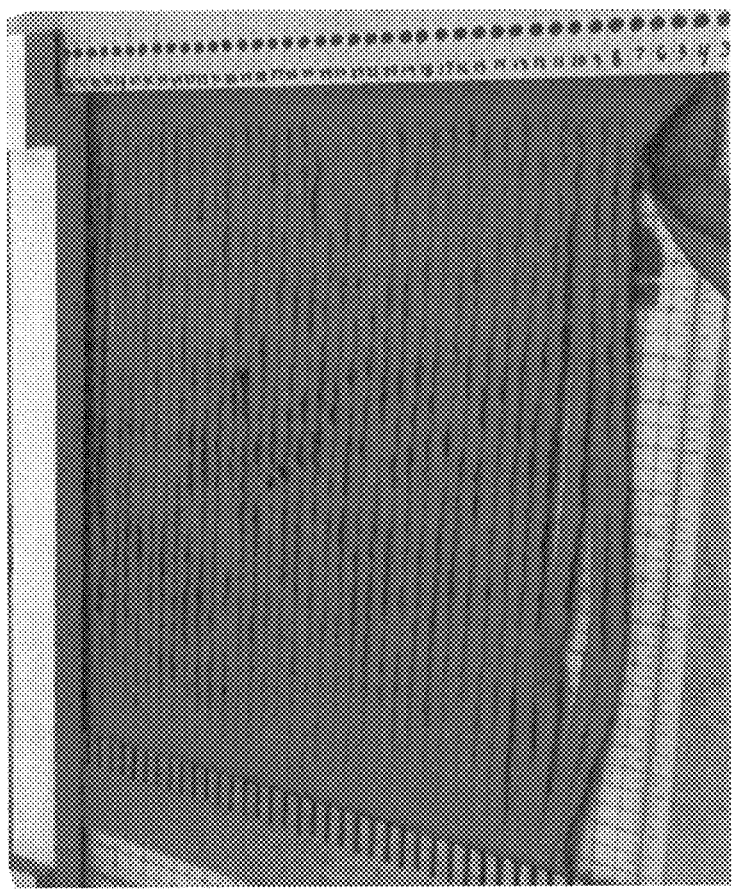
FIG. 11A shows the shirt mounted on the shirt cutting jig cut into multiple strips.

FIG. 11A shows shirt 80 cut into multiple strips.

Upon completion of cutting the shirt into multiple strips, cutting fence 50 is removed, and clamping bar 30 and clamping comb 40 are loosened to allow the user to remove the now-cut shirt from the jig.

Figure 11B:
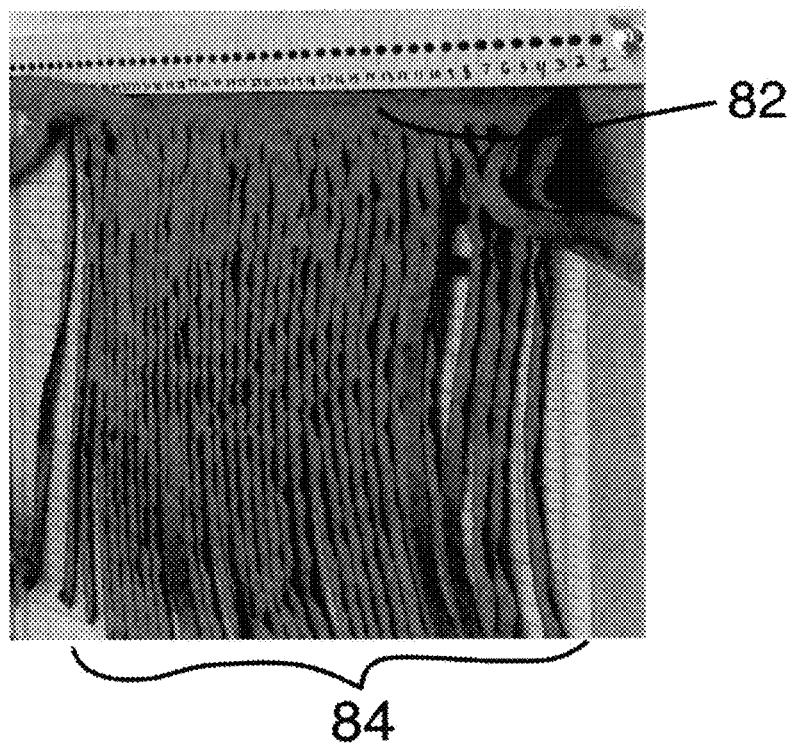
FIG. 11B shows the shirt partially removed from the shirt cutting jig, revealing the multiple cut strips of the shirt.

FIG. 11B shows the fully cut shirt partially removed from the jig.

As shown in FIG. 11B and in accordance with the present invention, the shirt includes multiple strips in which all the strips are connected along the shirt's first edge 82, and unconnected (i.e., cut) along the shirt's second edge 84.

At this point, the strips at the two ends of the shirt may be removed, if desired. For instance, each end may be relatively uneven or relatively wide as compared to the other strips, and thus their removal will result in strips of shirt that are the same or nearly the same in width. If the ends are acceptable, that is, are relatively straight and have widths that are similar to the widths of the other strips, then the ends do not have to be removed.

Figure 11C:
FIGS. 11C and 11D illustrate cutting of strips of material at the two ends of the shirt.
Figure 11D:
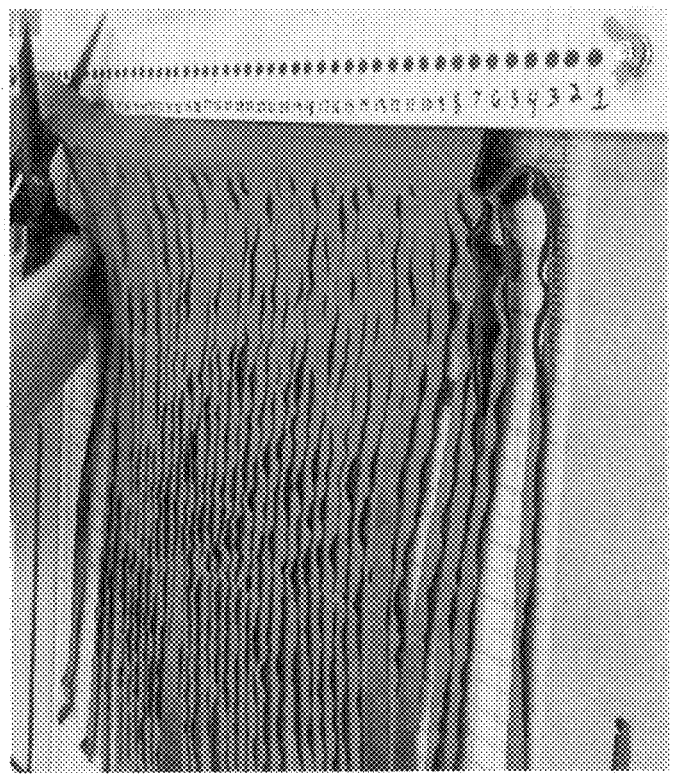

FIGS. 11C and 11D illustrate cutting of the strips of material at the two ends of the shirt.

Figure 11E:
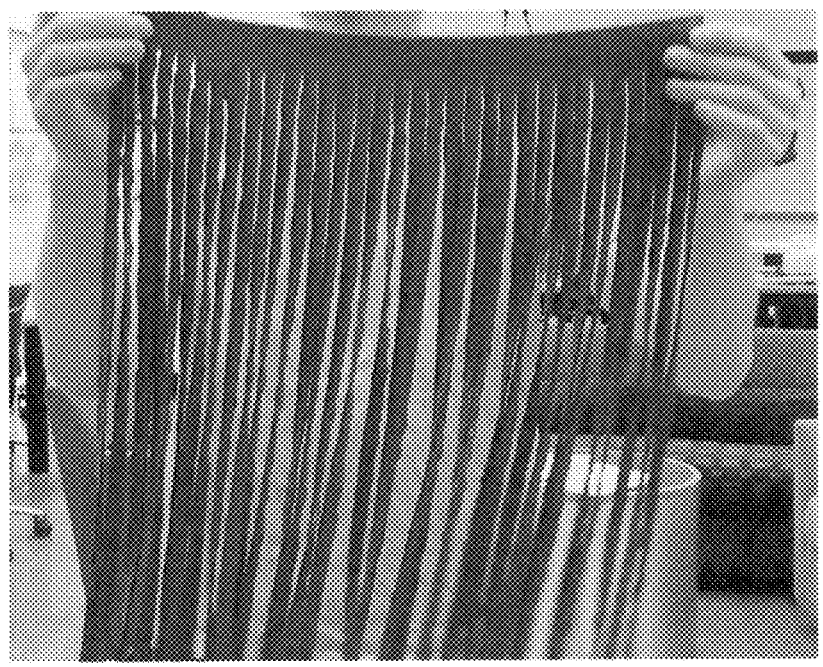
FIG. 11E shows the shirt, fully removed from the shirt cutting jig, cut into multiple strips.

FIG. 11E shows the shirt with the two ends trimmed off, revealing a shirt with strips of material that are identical or nearly identical in shape and size. The top of the cut shirt shown in FIG. 11E is the uncut folded edge 82.

Figure 12A:
FIGS. 12A through 12G are used to describe the remaining set of cuts to convert the cut shirt into a single long strip of material.

At this point, the shirt is ready for the final set of cuts. Initially, the uncut edge 82 of the shirt is opened as shown in FIG. 12A to allow that edge to be cut in a diagonal pattern to be described. Each of the remaining cuts is relatively short in length (as compared to the prior cutting along cutting fence 50). Any suitable cutting tool, such as a cutting roller or a scissor, may be employed for the remaining cuts.

Figure 12B:
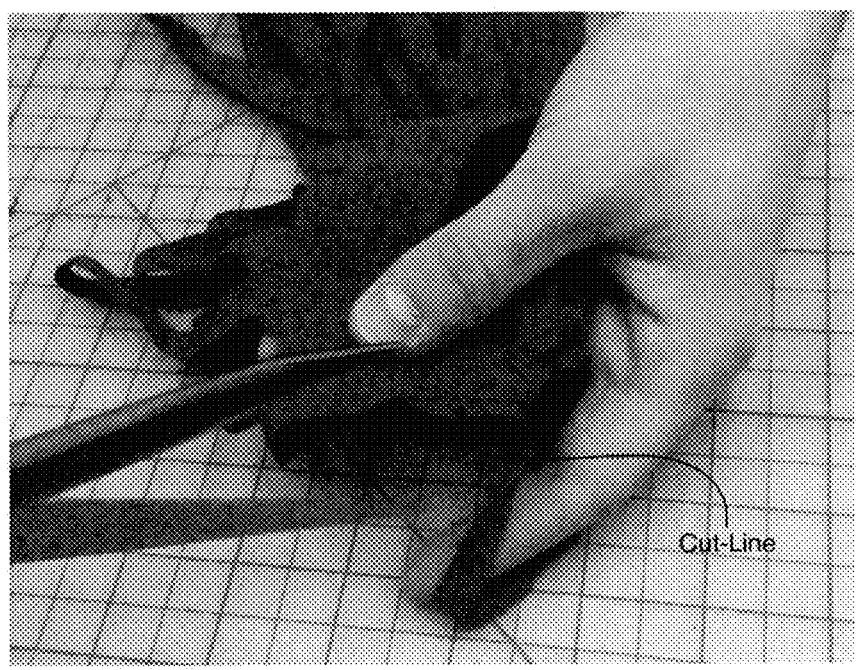

A first "diagonal cut" is made along the dotted lines shown in FIG. 12B below to create the start of a long strip of material. In FIG. 12B, the dashed line represents the cut-line, that is, the cut to be made by the cutting tool (e.g., the scissor shown in FIG. 12B).

Figure 12C:
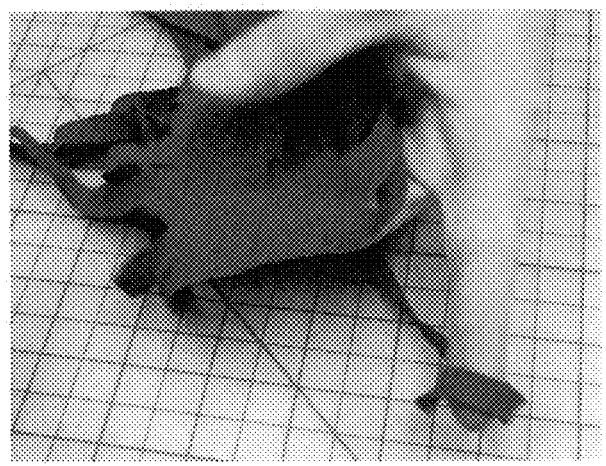
Figure 12D:
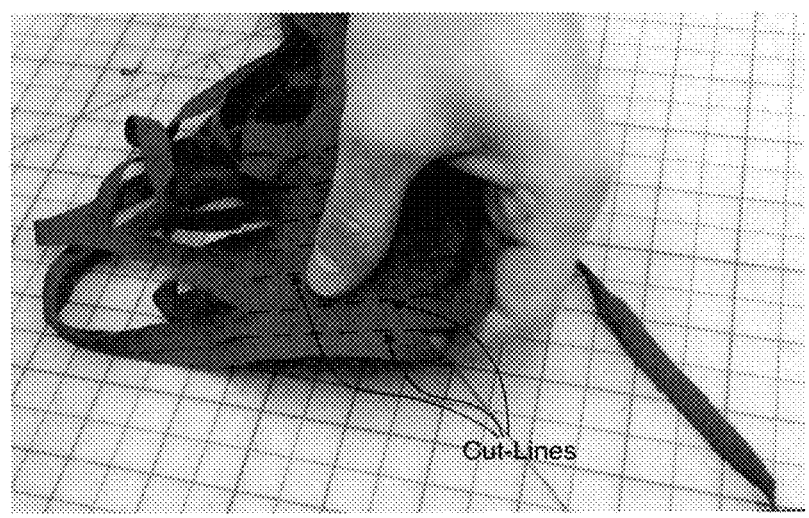
Figure 12E:
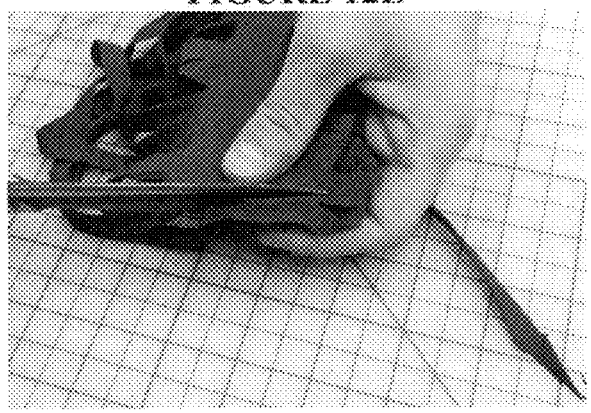
Figure 12F:
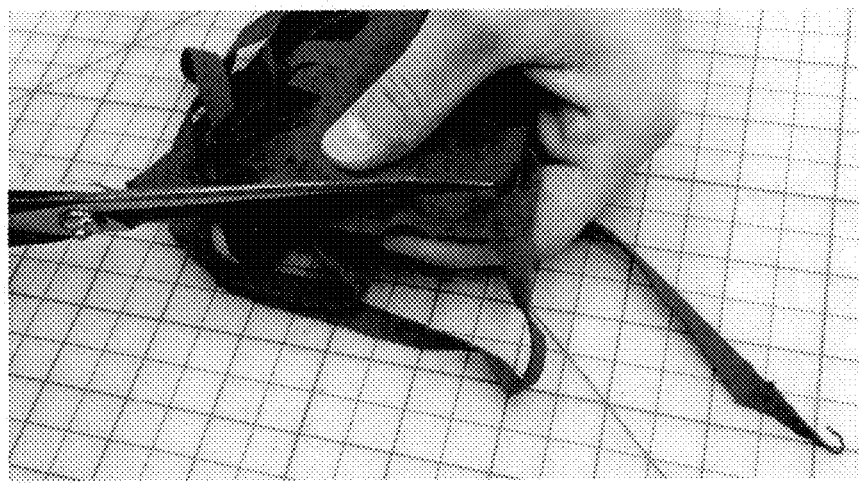
Figure 12G:
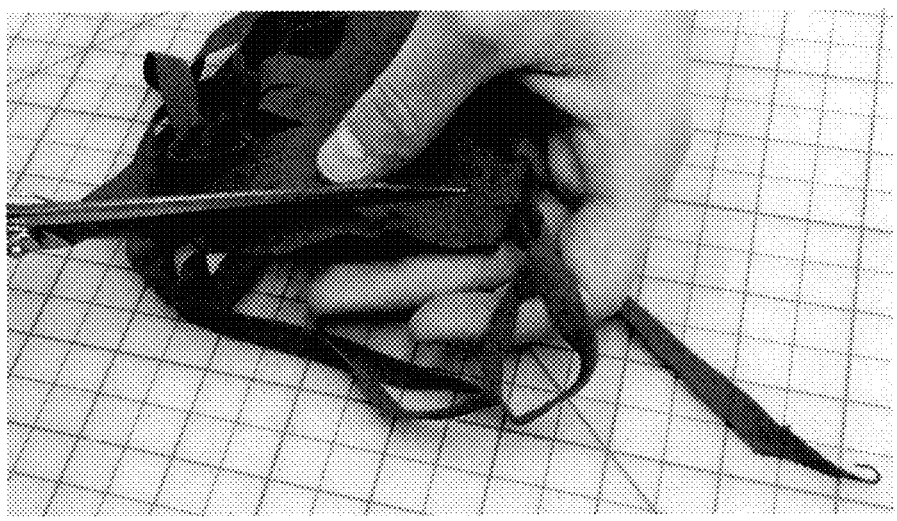

FIG. 12C shows a portion of the shirt after the first diagonal cut. Then, subsequent "diagonal cuts" are made along the "cut-lines" shown in FIG. 12D. FIG. 12E shows the cutting of the second diagonal cut using a scissor. FIG. 12F shows the cutting of the third diagonal cut. FIG. 12G shows the cutting of the fourth diagonal cut.

Figure 13A:
FIGS. 13A and 13B are used to describe converting the single, long strip of material into usable yarn.

Subsequent diagonal cuts are made until all the strips of material of the shirt have been cut to produce a very long single strip. FIG. 13A shows the resulting very long single strip. Additional details of converting the cut shirt with the configuration shown in FIG. 11E into a single, long strip of material are disclosed in the articles "How to make t-shirt yarn for knitting or crochet," published in Mollie Makes on Mar. 12, 2018, "How to Make T-Shirt Yarn," published in the Spruce Crafts on Dec. 8, 2018, "How to make your own T-shirt Yarn," published in Svellerella in 2014, and "Look at what I made," published in January 2016, and each of these published articles are incorporated herein by reference.

Figure 13B:

Finally, with such very long strip of material, the entire strip is pulled portion by portion through one's hands, which causes the material to curl in on itself, to create a tube shape, as shown in FIG. 13B.

Upon pulling the entire strip in this way, the shirt is converted into a long piece of yarn. The resulting yarn then may be used to make any number of products, such as rugs, dish cloths, sweaters, hats, and other clothing and non-clothing products.

While the invention has been shown and described with reference to certain embodiments of the present invention thereof, it will be understood by those skilled in the art that various changes may be made without departing from the spirit and scope of the invention.

For example, the dimensions presented herein are illustrative. That is, the size of the jig and/or the distance between the mounting apertures of the support and clamping bars, as well as the distance between the cutting apertures of the clamping comb, may be different than that described herein or shown in the figures. In particular, it may be desirable to provide a spacing between the mounting apertures and the cutting apertures to allow for the creation of strips that are narrower (or wider) than would be created by a 1 cm spacing.

As another example, a shirt may be cut into thicker strips of material by moving the cutting fence two spaces over (e.g., from position "7" (on the support bar and the clamping bar) to position "9") after cutting each strip of the shirt while carrying out the herein-described inventive process. If desired, the cutting fence can be moved three or more spaces over after each cut.

In accordance with another embodiment of the invention, a second clamping bar is utilized in place of a clamping comb. In such embodiment, both folded edges of the shirt will remain uncut after carrying out the process described herein. But then, after using the jig but before making the diagonal cuts as described herein, the user can manually cut (e.g., using a scissor, a cutting roller, or other suitable cutting device) the remaining small uncut pieces of each strip of one of the uncut folded edges. Thereafter, the other remaining uncut folded edge is cut using diagonal cuts as described above.

In accordance with a further embodiment of the invention, clamping bar 30 is replaced with two separate components, each serving a different function. That is, in the embodiment shown in the figures, the clamping bar serves the first function of supporting one end of the cutting fence and serves the second function of holding one of the folded edges of the shirt to the jig's base. In this further embodiment, a separate bar (with suitable mounting apertures), similar to support bar 20, is employed to carry out the first function of supporting the cutting fence. Then, a separate device, such as a second clamping panel (without the comb structure), is employed to secure the shirt's folded edge to the base.

In accordance with yet a further embodiment, clamping bar 30 is replaced with a second clamping comb that allows for the ends of the shirt under such second clamping comb to be cut. In such embodiment, separate strips of material are created after each cut during use of the jig. Each strip of material represents a tubular strip that may be converted into a tubular piece of yarn by pulling the material through one's hands, such as described above. Accordingly, with such embodiment, a shirt may be quickly cut using the jig to produce multiple, individual (i.e., separated) strips of material (each representing a tubular strip of material) that, in turn, are easily convertible into multiple loops of yarn. The loops of yarn then may be utilized as desired. For instance, certain craft projects employ loops of yarns, such as to create a woven potholder. For instance, the article "How to Make a Woven Potholder," published in 2018 by A and J Hobby Workshop, which is incorporated herein by references shows how to make a woven potholder from loops of material.

The loops of material or loops of yarn created during use of the jig in accordance with this embodiment may be employed for any desired purpose. Still further, if desired, each of the loops of material or loops of yarn may be easily cut to produce strips (non-loops) of material or yarn. In accordance with yet another embodiment of the present invention, the shirt stop on the base is omitted altogether. In such embodiment, the clamping bar may be rectangular in shape and is fully disposed on the base. The clamping bar, without the use of a shirt stop, still serves to both support the cutting fence and secure one edge of the shirt to the base as described herein.

For each of the embodiments (and variations thereof) described herein, other types of textiles/clothing may be employed in accordance with the present invention so long as such other clothing/textiles are tubular in shape or have portions that are tubular in shape. For instance, any of the following may be employed: the leg of a pair of pants, the arm of a long-sleeve shirt, a legging, a sock, a pillow case, and a fabric bag, to name several types of textile products.

The particular shape of the various components may be different than that shown in the figures. For instance, the cutting fence is shown to be a T-shaped structure, but the cutting fence may have a different structure so long as it can be mounted on the base at different positions and serve as a guide or straight-edge for a cutting tool to assist in cutting the shirt in multiple strips, as herein-described. As another example, the clamping panel can have a different structure and/or look different than the clamping comb 40 shown in the figures so long as it has multiple cutting apertures to enable a cutting tool to fully cut strips of material past the folded edge that is disposed beneath it. As a further example, clamping bar doesn't have to be L-shaped.

The positions of certain components may be different than that shown in the figures. For instance, the connecting hardware (for 30 and/or 40) can be at other appropriate/acceptable locations.

PARTS LIST

The following Table 1 is a parts list that identifies the components in the figures discussed herein. This parts list is provided solely for convenience and is not intended to limit the invention solely to these components.

TABLE 1

| Parts List | |
| --- | --- |
| Part | Element |
| Shirt Cutting Jig | 1 |
| Base | 10 |
| Shirt Stop Bar | 12 |

TABLE 1-continued

Parts List

| Part | Element |
| --- | --- |
| Cutting Surface | 14 |
| Slots | 16 |
| Support Bar | 20 |
| Mounting Apertures (of Support Bar) | 22a, 22b |
| Markings (on Support Bar) | 24a, 24b |
| Clamping Bar | 30 |
| Mounting Apertures (of Clamping Bar) | 32a, 32b |
| Markings (on Clamping Bar) | 34a, 34b |
| Connecting Hardware | 36, 42 |
| Bolt | 36a, 42a |
| Wingnut | 36b, 42b |
| Spring | 36c |
| Recess | 36d |
| Pins (of Clamping Bar) | 38 |
| Clamping Panel (Clamping Comb) | 40 |
| Teeth (of Clamping Comb) | 44 |
| Pins (of Clamping Comb) | 46 |
| Cutting Apertures | 48 |
| Cutting Fence | 50 |
| Mounting Ends (of Cutting Fence) | 52, 54 |
| Center Body (of Cutting Fence) | 56 |
| Pins (of Cutting Fence) | 58a, 58b |
| Shirt | 60, 70, 80 |
| Shirt Edge | 60a |
| Tubular Lower Portion (of Shirt) | 72 |
| Top Portion (of Shirt) | 74 |
| Sleeves (of Shirt) | 76 |
| Lower Edge (of Shirt) | 78 |
| Folded Edges (of Shirt) | 82, 84 |
| Open Ends (of Shirt) | 83, 85 |
| Cut Strips | 86A, 86B |
| Cutting Roller | 90 |

Having described the present invention including various features and variations thereof, it is intended that the appended claims be interpreted as including the embodiments described herein, the alternatives mentioned above, and all equivalents thereto.

What is claimed is:

1. A process for converting a textile into yarn, comprising the steps of:
   providing a jig, the jig having a base, a clamping bar, a comb-shaped clamping panel and a cutting fence;
   mounting a tubular body of a textile flat on a top surface of the base of the jig, the tubular body mounted on the base having first and second folded edges and first and second open ends;
   securing, to the base, the clamping bar over the first folded edge of the tubular body to secure the first folded edge to the base;
   securing, to the base, the clamping panel over the second folded edge of the tubular body to secure the second folded edge to the base, and wherein securing includes positioning the clamping panel relative to a position of the second folded edge of the tubular body so that a plurality of teeth of the clamping panel extend onto the tubular body and portions of the second folded edge are accessible within gaps disposed between the teeth;
   mounting the cutting fence on the jig at a first position extending from the clamping bar to the clamping panel;
   cutting, using the cutting fence as a cutting guide, a strip of material of the tubular body, the cut strip of material extending from the second folded edge of the tubular body to a position adjacent to but not extending fully to the first folded edge;
   repositioning the cutting fence on the jig by mounting the cutting fence to a position adjacent to the cutting fence's prior position, the repositioned cutting fence extending from the clamping bar to the clamping panel;
   repeating the cutting and repositioning steps multiple times until a substantial portion of the tubular body is cut into multiple strips of material;
   removing from the jig the tubular body with the multiple strips of material;
   opening the tubular body with the multiple strips of material at the first folded edge;
   cutting, at the opened first folded edge, each of the strips of material in a diagonal pattern to produce from the tubular body a single strip of material;
   converting the single strip of material into a single strip of yarn.

2. The process of claim 1, wherein securing the clamping bar comprises moving the clamping bar from a raised position above the base to a lowered position adjacent to the base; and securely holding the tubular body by a plurality of pins extending downwardly from the clamping bar when the clamping bar is moved adjacent to the base.

3. The process of claim 2, wherein the base includes a stop bar; the process comprising positioning the tubular body so that its first folded edge is immediately adjacent to the stop bar of the base whereupon the first folded edge is positioned beneath the clamping bar and securely held when the clamping bar is moved to the lowered position.

4. The process of claim 1, wherein securing the clamping panel comprises first positioning the clamping panel at a position on the base to accommodate a size of the tubular body; and then securing the clamping panel to the base over the second folded edge of the tubular body.

5. The process of claim 1, wherein securing the clamping panel comprises moving the clamping panel from a raised position above the base to a lowered position adjacent to the base; and securely holding the second folded edge of the tubular body by a plurality of pins extending downwardly at ends of the plurality of teeth of the clamping panel.

6. The process of claim 1, wherein mounting the cutting fence comprises mounting a first end of the cutting fence on the clamping bar and mounting a second end of the cutting fence on a support bar that is mounted on the base at a position opposite the clamping bar.

7. The process of claim 1, comprising providing a shirt with sleeves; and removing the sleeves from the shirt to produce the tubular body.

8. A jig for converting a textile into yarn, comprising:
   a base configured to support a tubular body of a textile, the base having a first side and a second side opposite the first side;
   an elongated support bar secured to a top of the base at or near the first side of the base, the support bar including a plurality of mounting apertures;
   an elongated clamping bar configured to be secured to the top of the base at or near the second side of the base in order to secure a first folded edge of the tubular body to the base, the clamping bar including a plurality of mounting apertures;
   a clamping panel having a plurality of teeth and configured to be secured to the top of the base, between the support bar and the clamping bar, in order to secure a second folded edge of the tubular body to the base; and
   a cutting fence mountable to and extending between the support bar and the clamping bar using the mounting apertures of the support bar and the clamping bar, and configured to be movable along the support bar and the clamping bar to enable cutting of the tubular body mounted on the base into a body having multiple strips of material configured to be converted into usable yarn.

9. The jig of claim 8, wherein the clamping bar includes a plurality of pins extending downwardly towards the base and configured to secure the first folded edge of the tubular body to the base.

10. The jig of claim 9, wherein the base includes a stop bar; and the clamping bar is configured to be secured to the stop bar of the base, and the plurality of pins of the clamping bar are positioned adjacent to the stop bar when the clamping bar is secured to the stop bar.

11. The jig of claim 8, wherein the clamping panel is configured to be movable along and secured to the base at a selectable position to accommodate a tubular body of different sizes.

12. The jig of claim 8, wherein at least some of the plurality of teeth of the clamping panel include downwardly extending pins configured to securely hold the second folded edge of the tubular body to the base when the clamping panel is secured to the base.

13. The jig of claim 8, wherein apertures between the teeth of the clamping panel are sized to allow a cutting tool to be used to cut the tubular body completely to an end of the second folded edge.

14. The jig of claim 8, wherein the cutting fence includes first and second mounting ends and a center body disposed between the first and second mounting ends, each of the first and second mounting ends including a respective pin configured to be placed within a respective mounting aperture of the support bar and the clamping bar.

15. The jig of claim 14, wherein the mounting apertures of the support bar and the clamping bar are spaced along the support bar and the clamping bar, respectively, at equal intervals, and the cutting fence is configured to allow the pins of the first and second mounting ends to be placed within corresponding, respective mounting apertures of the support bar and the clamping bar.

* * * * *